US011579160B2

(12) United States Patent
Muschler et al.

(10) Patent No.: US 11,579,160 B2
(45) Date of Patent: *Feb. 14, 2023

(54) SYSTEMS AND METHODS FOR DETECTION, ANALYSIS, ISOLATION AND/OR HARVESTING OF BIOLOGICAL OBJECTS

(71) Applicants: THE CLEVELAND CLINIC FOUNDATION, Cleveland, OH (US); PARKER HANNIFIN CORPORATION, Cleveland, OH (US)

(72) Inventors: George F. Muschler, Cleveland Hts., OH (US); James K. Monnich, Greensburg, PA (US); Edward J. Kwee, Cleveland, OH (US); Kimerly A. Powell, Lake Forest Park, WA (US); Edward E. Herderick, Pickerington, OH (US); Cynthia A. Boehm, North Olmsted, OH (US); Thomas R. Adams, Cheswick, PA (US); Robert Germanoski, Jeannette, PA (US); Frank Krakosh, III, Latrobe, PA (US); James Dunn, Pittsburgh, PA (US); Daniel Bantz, Brookline, NH (US)

(73) Assignees: THE CLEVELAND CLINIC FOUNDATION, Cleveland, OH (US); PARKER INTANGIBLES LLC, Cleveland, OH (US)

(*) Notice: Subject to any disclaimer, the term of this patent is extended or adjusted under 35 U.S.C. 154(b) by 451 days.

This patent is subject to a terminal disclaimer.

(21) Appl. No.: 16/741,864

(22) Filed: Jan. 14, 2020

(65) Prior Publication Data

US 2020/0150143 A1 May 14, 2020

Related U.S. Application Data

(63) Continuation of application No. 15/309,712, filed as application No. PCT/US2015/029892 on May 8, 2015, now Pat. No. 10,564,172.

(Continued)

(51) Int. Cl.
*G01N 35/10* (2006.01)
*C12M 1/36* (2006.01)
(Continued)

(52) U.S. Cl.
CPC ........ *G01N 35/1011* (2013.01); *B01L 3/0262* (2013.01); *B01L 9/56* (2019.08);
(Continued)

(58) Field of Classification Search
CPC ........ G01N 35/1011; G01N 2035/1013; B01L 9/56; B01L 3/0262; B01L 2300/0654; C12M 41/48; G01B 11/0608; G01B 11/14
See application file for complete search history.

(56) References Cited

U.S. PATENT DOCUMENTS 5,978,498 A  11/1999  Wilhelm et al.
6,101,265 A   8/2000  Bacus et al.
(Continued)

FOREIGN PATENT DOCUMENTS

EP  1 502 649 A1  2/2005
EP  1 548 448 A1  6/2005
(Continued)

OTHER PUBLICATIONS

Uber, D. C., et al. "Application of robotics and image processing to automated colony picking and arraying." BioTechniques 11.5 (1991): 642-647.

(Continued)

*Primary Examiner* — Benjamin R Whatley
(74) *Attorney, Agent, or Firm* — Tarolli, Sundheim, Covell & Tummino LLP

(57) ABSTRACT

Systems and methods provide for detection and controlled interaction with one or more objects. The system can include an imaging subsystem (20), a tool subsystem (26) containing one or more tools, a stage subsystem (16) and a control system (40). The control system (40) can integrate controls for each of the other subsystems, which controls can be implement desired functions over a variety of process parameters to perform the controlled interaction.

10 Claims, 15 Drawing Sheets

Related U.S. Application Data

(60) Provisional application No. 61/990,387, filed on May 8, 2014.

(51) Int. Cl.
*B01L 9/00* (2006.01)
*B01L 3/02* (2006.01)
*G01B 11/06* (2006.01)
*G01B 11/14* (2006.01)

(52) U.S. Cl.
CPC ......... *C12M 41/48* (2013.01); *G01B 11/0608* (2013.01); *G01B 11/14* (2013.01); *B01L 2300/0654* (2013.01); *G01N 2035/1013* (2013.01)

(56) References Cited

U.S. PATENT DOCUMENTS

| | | |
|---|---|---|
| 6,146,881 A | 11/2000 | Hering |
| 6,226,392 B1 | 5/2001 | Bacus et al. |
| 6,252,979 B1 | 6/2001 | Lee et al. |
| 6,466,690 B2 | 10/2002 | Bacus et al. |
| 6,674,881 B2 | 1/2004 | Bacus et al. |
| 6,674,884 B2 | 1/2004 | Bacus et al. |
| 6,775,402 B2 | 8/2004 | Bacus et al. |
| 7,092,557 B2 | 8/2006 | Eisfeld et al. |
| 7,146,372 B2 | 12/2006 | Bacus et al. |
| 7,218,764 B2 | 5/2007 | Vaisberg et al. |
| 7,310,147 B2 | 12/2007 | Jiang |
| 7,496,220 B2 | 2/2009 | Izzia et al. |
| 7,505,618 B2 | 3/2009 | Palsson et al. |
| 7,590,492 B2 | 9/2009 | Zahniser et al. |
| 7,738,730 B2 | 6/2010 | Hawley |
| 7,776,584 B2 | 8/2010 | Richmond et al. |
| 7,796,815 B2 | 9/2010 | Muschler et al. |
| 8,034,612 B2 | 10/2011 | Richmond et al. |
| 8,034,625 B2 | 10/2011 | Richmond et al. |
| 8,064,678 B2 | 11/2011 | Gregson |
| 8,068,670 B2 | 11/2011 | Muschler et al. |
| 8,218,840 B2 | 7/2012 | Eisfeld et al. |
| 8,293,520 B2 | 10/2012 | Richmond et al. |
| 8,293,525 B2 | 10/2012 | Richmond et al. |
| 8,293,526 B2 | 10/2012 | Richmond et al. |
| 8,293,527 B2 | 10/2012 | Richmond et al. |
| 8,417,011 B2 | 4/2013 | Klottrup et al. |
| 10,564,172 B2 * | 2/2020 | Muschler ............... G01B 11/14 |
| 2001/0019845 A1 | 9/2001 | Bienert et al. |
| 2003/0179916 A1 | 9/2003 | Magnuson et al. |
| 2003/0219892 A1 | 11/2003 | Palsson et al. |
| 2004/0236773 A1 * | 11/2004 | Bacus .................. G02B 21/367 |
| 2005/0254696 A1 | 11/2005 | Bacus et al. |
| 2008/0267486 A1 | 10/2008 | Van Slyke |
| 2010/0074507 A1 | 3/2010 | Klottrup et al. |
| 2010/0165326 A1 | 7/2010 | Tomisek et al. |
| 2011/0124037 A1 | 5/2011 | Backhaus et al. |
| 2012/0074507 A1 | 3/2012 | Jo et al. |
| 2013/0205920 A1 | 8/2013 | Tow |

FOREIGN PATENT DOCUMENTS

| | | |
|---|---|---|
| EP | 1 502 649 B1 | 12/2007 |
| EP | 1 754 537 B1 | 6/2010 |
| WO | WO 2005/121746 A1 | 12/2005 |
| WO | WO 2008/034868 A2 | 3/2008 |
| WO | WO 2011/153526 A2 | 12/2011 |
| WO | WO 2012/129105 A1 | 9/2012 |

OTHER PUBLICATIONS

Jones, Peter, et al. "Integration of image analysis and robotics into a fully automated colony picking and plate handling system." Nucleic acids research 20.17 (1992): 4599-4606.
RoboSep Product webpage, accessed Mar. 30, 2017.
ALS Automated Lab Solutions GmbH CellCelector webpage, accessed Apr. 4, 2017.
Automate.it pixcell brochure, www.paa-automation.com, accessed Dec. 8, 2016.
STEMvision Automated Colony-Forming Cell Assay Reader Technical Manual, www.stemcell.com, accessed Dec. 8, 2016.

* cited by examiner

Original Colony Object

Original Harvest Strategy

Documentation Image

Updated Harvest Strategy

SYSTEMS AND METHODS FOR DETECTION, ANALYSIS, ISOLATION AND/OR HARVESTING OF BIOLOGICAL OBJECTS

CROSS-REFERENCE TO RELATED APPLICATION

This application is a continuation of U.S. application Ser. No. 15/309,712, filed Nov. 8, 2016, and entitled SYSTEMS AND METHODS FOR DETECTION, ANALYSIS, ISOLATION AND/OR HARVESTING OF BIOLOGICAL OBJECTS, which is a 371 of PCT App. Ser. No. PCT/US2015/029892, filed May 8, 2015, and entitled SYSTEMS AND METHODS FOR DETECTION, ANALYSIS, ISOLATION AND/OR HARVESTING OF BIOLOGICAL OBJECTS, which claims the benefit of priority from U.S. Provisional Patent Application No. 61/990,387, filed May 8, 2014, and entitled AUTOMATED SYSTEM AND METHOD FOR DETECTION, ISOLATION AND HARVESTING OF BIOLOGICAL OBJECTS. Each of the above-identified applications is incorporated herein by reference in its entirety.

BACKGROUND

Systems exist to provide for the automatic selection and harvesting of cells and cell colonies. Such systems involve various levels of automation. Such systems can also utilize current selection algorithms to facilitate the screening and harvesting of clone cells for a wide range of cell types and development of cell lines. While advancements continue to be made in such systems, further automation and improved accuracy is desirable.

DETAILED DESCRIPTION

This disclosure relates to automated systems and methods for detection, sequential analysis, isolation and/or harvesting of biological objects. The system can include an imaging subsystem, a tool subsystem, a stage subsystem and a control system. The control system can integrate controls for each of the other subsystems, which controls can be interdependent to implement desired functions over a variety of process parameters.

As an example, a method can include identifying at least one object of interest based on image data representing the object of interest residing in medium, such as acquired by the imaging system. An image analysis function, which can be part of the control system or include separate analytics, can be configured to analyze the acquired image data to determine a distribution of pixels or voxels of an image that corresponds to the object of interest. The control system can control one or more forms of interaction with the object of interest based on the distribution of pixels or voxels. The control can further be updated dynamically during the interaction based on image data acquired during such interaction to enable corresponding adjustments to one or more of the controls.

The tool system may include tools that are used to interact with the medium or interact directly with the biological object. The interaction with the medium may include addition or removal of medium elements resulting in a change in composition of the medium. The interaction with the medium may also include mechanical or biophysical modification of the medium conditions such as through movement, agitation, heating, cooling or application of external biophysical stimuli (e.g. light energy or electromagnetic fields). Interaction can also include use of a tool having an interior space through which fluid or medium may flow, and the use of this tool to locate and aspirating medium using a fluidic system. Interaction, including but not limited to aspiration, may be used to sample, harvest, move, remove or kill biological objects (e.g., cells or colonies of cells) or other material that may complicate or hinder the effectiveness of the interaction with the object. As another example, the interaction can include acquiring one or more images, which can be analyzed to determine information and process parameters. Images taken at two points in time may also be used to detect and measure changes that have taken place in the biological object or objects as a result of the interaction.

Figure 1:
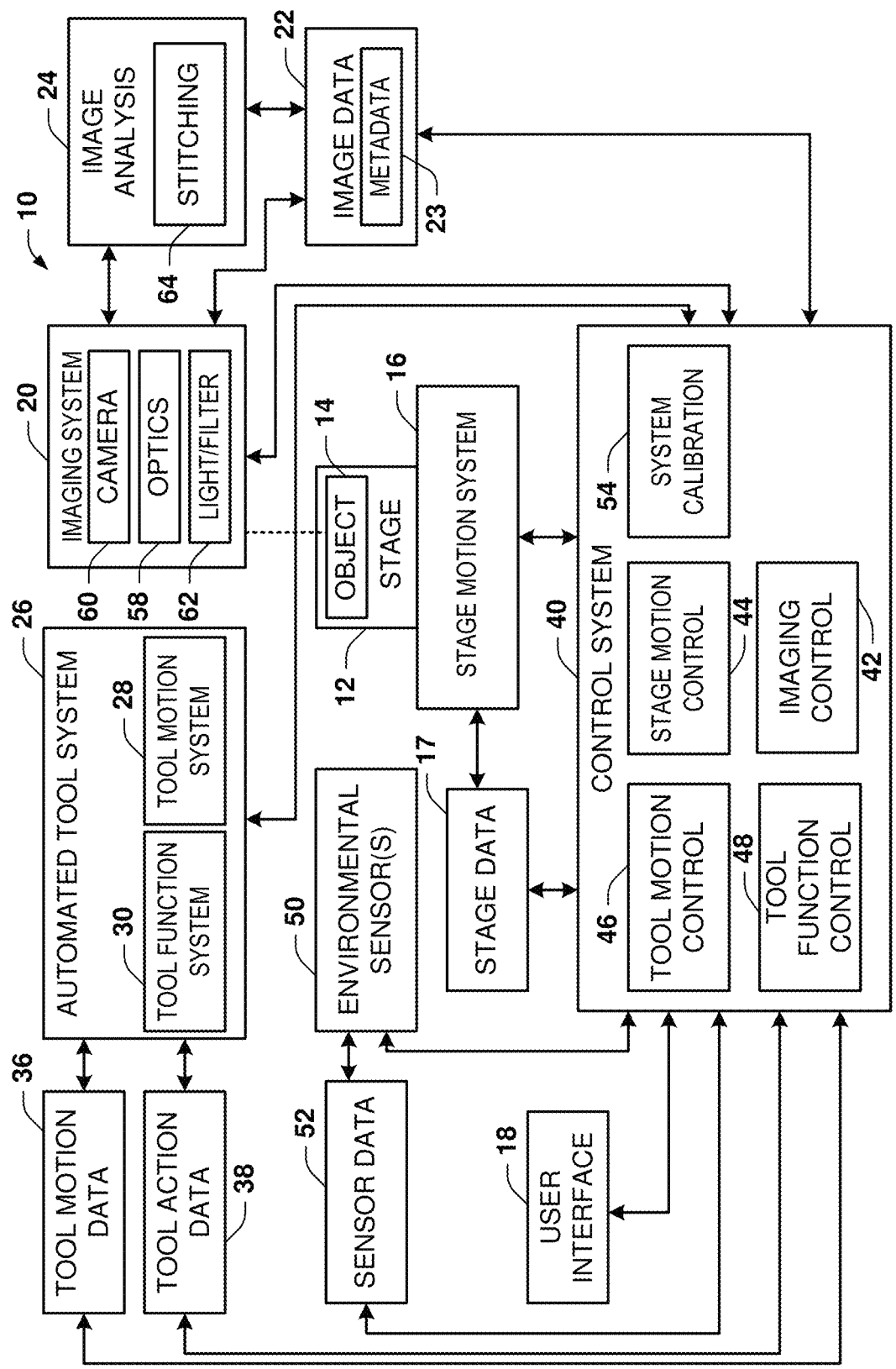
FIG. 1 depicts an example of a block diagram of a system to facilitate detection, isolation and harvesting of biological objects.

FIG. 1 depicts a block diagram of an example of an automated system 10 for detection, sequential analysis, isolation and harvesting of objects. As used herein, the object being harvested can correspond to a cell, a group of cells including a colony or a collection of cells corresponding to a population of cells, or cells forming a tissue. While many examples herein describe the objects as including cells or colonies of cells, it is to be understood and appreciated that the system and methods are not limited in application to cells as images of other types of objects can also be processed according to an aspect of the present invention. For example, the objects can also include microorganisms (e.g., bacteria, protozoa), cell nuclei, cell organelles, viruses, non-biological structures (e.g., proteins, peptides or glycoproteins), different constituent parts of such objects or any combination of one or more of such objects.

In order to control process parameters, the system 10 includes a control system 40 that is programmed to control the various subsystems of the system including a stage motion system 16, imaging system 20, and the automated tool system 26 (e.g., further including tool function system 30 and tool motion system 28). Thus, in the example of FIG. 1, the control system 40 includes an imaging control 42, stage motion control 44, tool motion control 46 and tool function control 48. The control system 40 provides an integrated control method to coordinate control of the various system components 20, 26 and 16 to perform a variety of functions, as disclosed herein. While in the example of FIG. 1 for purposes of explanation each of the respective control blocks 42, 44, 46 and 48 are demonstrated as separate modules (e.g., program code blocks executable by a processor), it is to be understood that the methods and functions implemented by such controls can be integrated and interdependent to effect desired isolation detection and harvesting of biological objects.

In the example of FIG. 1, the system 10 includes a stage 12 that supports the objects of interest 14. The position and movement of the stage 12 in a defined stage coordinate system can be controlled by a stage motion system 16. The stage motion system 16 can include an arrangement of motors connected to drive the stage 12 to a desired position in accordance system based on profits parameter. For example, the stage motion system 16 can include an arrangement of linear motors configured to adjust the position of the stage 12 along two or more (e.g., three) orthogonal axes, corresponding to X and Y axes.

The objects 14 that are positioned on the stage can correspond to plated cells residing in a known medium, such as can be a liquid medium or a viscous or solid (e.g., alginate, methycellulose, hyalyonan, or other hydrogel composed of natural or synthetic polymeric gel materials or the like). One or more types of marker criteria can be utilized to differentiate or optically label structures and/or chemical features of objects in a given image. Examples of some marker criteria include staining (e.g., with one or more dyes), employing phase contrast microscopy, topographic image mapping of a two-dimensional surface. Additionally or alternatively, for various types of cells the marker criteria can include an immunochemical marker, a histochemical marker, as well as an in situ hybridization marker. Those skilled in the art will understand and appreciate particular applications of these and other types of marker criteria that can be used to optically identify objects and/or chemical features of objects in an image.

By way of example, AP staining can be employed as a mechanism to analyze undifferentiated progenitor cells, for example. AP and DAPI stains can be utilized together on a given sample, such as for locating cells (e.g., via DAPI or other staining) as well as analyzing performance characteristics of certain types of cells (e.g., via AP or other staining). It is to be appreciated that other stains or dyes can also be utilized in addition to or as an alternative to AP and/or DAPI staining. The particular types of staining employed can vary according to the types of objects being selectively stained. For example, specific types of cells, different components within cells (e.g., organelles, proteins or other molecules) as well as other objects can be selectively stained and provided as the one or more objects of interest.

Markers can also be employed to identify (e.g., via image analysis 24) chemical features or morphologic features in the matrix materials around and near the cells, which further can be used to characterize and assess biological identity or performance of the adjacent cells. For example, chemical features may include proteins or other chemical compounds that may be secreted or deposited by cells. Morphologic features near the cells can include supercellular features (e.g., collections of cells into geometric structures, such as tubular and rosette shapes), minerals (e.g., calcium-based compounds) formed near the cells, fibrous proteins formed near cells, as well as the size and configuration of junction points between cells to name a few. Other morphological features can include physical features of cells or groups of cells, such as including size, shape, optical density, autofluorescence, presence of absence of cell surface markers, presence or absence of specific extracellular matrix components and/or presence of specific enzymatic activity. Additionally, groups of cells can be identified as functionally related to one another as a biologically relevant group (e.g., a group of cells likely sharing a common ancestral cells (colonies), or a group of cells responding (or not) to a specific signal, cells meeting (or not meeting) metrics defining a desired range or constellation of features).

The medium can be a standard medium or it can be user selected and information about the medium (e.g., material properties, optical properties and the like) can be entered into the system 10 via a corresponding user interface 18. The user interface 18 can be programmed to provide a human machine interface through which one or more users can interact with the system 10. Such human-machine interactions by the user can include setting operating parameters and thresholds utilized by the system. The human-machine interactions can also include remotely controlling the positioning of the stage along one or more of its axes. The user interface 18 can also be employed to define properties, interaction protocols, and/or process parameters associated with the objects, the medium for the objects or other parameters or criteria that can be utilized in conjunction with the detection isolation and/or harvesting of the objects from the stage 12.

The imaging system 20 is configured to acquire image data 22 that includes one or more images collected from the stage. As used herein, the images can be static images captured at an instantaneous time and/or video images captured over a time interval. By way of example, the imaging system 20 can include a digital camera 60, such as can include an arrangement of one or more digital sensors, analog sensors, charge coupled device (CCD) sensor, complementary metal oxide semiconductor (CMOS) sensor, charge injection device (CID) sensor. The arrangement of optical sensors may be implemented as a two-dimensional array. The one or more sensors, for instance, can be implemented in a digital camera 60 or the sensors could be a special purpose imaging device. The imaging system 20 provides an output signal corresponding to image data in response to detecting light (e.g., visible and/or non-visible light). The imaging system 20 can be configured to operate in an automated manner to acquire images of the stage and store corresponding image data over a period of time.

In the example of FIG. 1, the imaging system 20 is demonstrated as also including optics 58 that can control the field of view and resolution. The imaging system can also include one or more lights and/or filters 62 that can be utilized to change the type of illumination and/or filters applied for removing selected wavelengths of the illuminated light from the image being captured by the camera 60. The optics 58 can be selected to refine an object field of view but in turn can be passed to the camera 60 for capturing the corresponding digital image.

For example, the camera 60 can be implemented as a digital camera that can be attached to a microscope containing the optics 58 for capturing at least a portion of the field of view as pixels having values that collectively form a corresponding digital image that is stored as the image data 22. For each image that is stored in the image data 22, the control system 40 can include metadata with the image data specifying parameters of the imaging system 20, such as image resolution, time and date information, the associated optics setting(s) as well as an indication of the light source and/or filtering that is utilized for the captured image.

Additionally, the control system 40 can provide location information in the metadata 23 that represents other state parameters for the system, including a spatial location (e.g., in stage coordinates in two or more dimensions) for each captured image. For example, the location metadata for each image can represent the spatial coordinates of the stage at a time when each respective image is acquired, such as corresponding to or derived from linear position encoders that provide absolution position for the stage along its respective axes. Additionally or alternatively, the location coordinates can be stored in the metadata 23 to identify the spatial position in stage coordinates that has been converted to an image coordinate for one or more predetermined pixels (e.g., at a center, along a perimeter or other locations) in the captured image, such as by registering the spatial coordinates of the stage to a predetermined location or other marker on the stage. Since the spatial location of the stage is known for each image (e.g., from absolute encoder data provided by respective encoders in response to position of the stage) and an offset between the tool and at least one pixel in the field of view is also known with respect to stage coordinates, as disclosed herein, the stage can be moved relative to the tool, to accurately position the tool in alignment for interaction with an object in each respective image. For example, given a set of pixels of interest corresponding to a target object, the spatial offset between the tip of a tool and optical system can be employed to move the stage relative to the tip to position the tip in axial alignment with the target object. Other machine state information that can be part of the metadata 23 can include time, current position of all monitor components (e.g., from respective position encoders).

As a further example, the imaging system 20 can be configured to acquire a temporal sequence of images for a localized set of one or more cells/colonies at defined time intervals. Such serially acquired images can be used to identify changes that occur between two or more serial images. The identified changes can be interpreted as biological events of functional significance (e.g., proliferation, migration, change in physical, chemical, anabolic, catabolic or secretory properties) at the level of an individual cell or at the colony level, for example.

The image data 22 can include values for pixel or voxels in each image as well as process related data and/or metadata, such as timestamps, temperature, pressure, medium conditions, and the like. An image analysis module 24 can be programmed to apply preprogrammed analytics to analyze and evaluate the imaging data that is acquired to enable detection and isolation of the biological objects of interest. An example of an image analysis that can be utilized is shown and described in U.S. Pat. No. 8,068,670, which is incorporated herein by reference. The '670 patent also discloses an approach for stitching a spatially contiguous sequence of images together to create a corresponding montage image that includes a plurality of adjacent field of views. Metadata, including spatial coordinates, can be stored with each of the individual images that have been stitched together to form the corresponding montage image to facilitate interaction with objects that may be identified at different parts of the montage image.

The pixels or voxels for a given image can represent imaging data acquired by the imaging system 20 from one or a plurality of imaging domains or imaging modalities (e.g. bright field microscopy, phase contrast, Numarski imaging, fluorescence microscopy, or the like). Such multimodal imaging parameters can enable changes in individual and collective objects to be measured, for example, with respect to transmitted light, phase contrast, fluorescence, and other spectral features. Thus, the image analysis 24 can employ a mathematical algorithm to integrate imaging data from one or more domains for characterization and interpretation of values in the pixels or voxels (e.g. a ratio of brightness or product of brightness). The image analysis 24 can also be configured to provide summary analysis reports itemizing features of individual cells, groups of cells and/or the relationship of individual cells to defined groups within each of the acquired images. The resulting analysis data can also be stored as part of the image data 22 to facilitate further isolation and harvesting of biological objects.

As a further example, the image analysis 24 can be programmed to quantify changes at the level of individual biological objects including, for example, with respect to attachment, migration, survival, metabolic activity, protein secretion, expression of surface markers, and/or morphological changes. Additionally or alternatively, the image analysis 24 can quantify changes at the level of the entire population of biological objects with respect to attachment, migration, survival, metabolic activity, protein secretion, expression of surface markers, and/or morphological changes.

The system 10 can also include the automated tool system 26 that is configured to interact with one or more selected objects 14 based on at least in part on the distribution of pixels or voxels that is part of the image data 22. The automated tool system 26 can be configured to position one or more tools in a location for interacting with medium or one or more of the biological objects 14 disposed on or in such medium. The automated tool system 26 further can include a tool motion system 28 that is configured to adjust the position of a tool or more than one tool relative to the stage 12. The tool motion system 28 can include an arrangement of linear motors, rotary motors and/or other types of actuators configured to control movement of the syringe and components that may be attached thereto, such as needles or various tip shapes, in three-dimensional space. For example, an arrangement of linear motors can be provided to enable precise positioning of the tool along three orthogonal axes.

An example of a device that can be implemented as the tool system 26 or at least a portion thereof is disclosed in U.S. patent application Ser. No. 13/701,853 (U.S. Pat. Pub. No. 20130129538), filed Feb. 7, 2013, and entitled MINIATURIZED SYRINGE PUMP SYSTEM AND MODULES, which is incorporated herein by reference in its entirety. The tool motion system 28 can move the tool, including a tip of such tool, along a z-axis that is orthogonal to the surface of the stage to enable interaction between the tip of the tool and the media and/or biological objects disposed thereon. Additionally or alternatively, the tool motion system 28 can move the stage along X and/or Y axes such as to provide for positioning the tool in three-dimensional space in response to control instructions from the control system to the motion system 28.

As a further example, the control system 40 can provide instructions, corresponding to motion data 36, to the motion system 28 to move the tool to a predefined location in the coordinate system of the corresponding tool having a predefined position (e.g., tool reference coordinates) in the coordinate system of the stage 12 (or to some other common coordinate system), which can be utilized for accurately positioning the one or more tools with respect to a target location identified in one or more images. Calibration disclosed herein between the tool system 26 and the image system 20 enables precise positioning of the tool with respective locations identified in captured images.

In order to enable such precise positioning of the tool, the control system 40 can implement a calibration function 54 for the system 10. For example, the system calibration function 54 can determine a spatial offset between a tip of a tool of the automated tool system 26 with respect to an optical location within the field of view of the imaging system 20. The spatial offset can be stored in memory and utilized by the control system 40 to position the stage 12, accurately and reproducibly, relative to the tip of the tool. As mentioned, the images can be stored in the image data 22 associated with corresponding metadata 23, including position metadata. Since the metadata 23 associated with each respective image can include a corresponding spatial position of the stage associated with one or more pixels thereof (e.g., a center pixel or a predetermined edge pixel), accurate coordinates of an object identified with respect to one or more pixel in the image can be readily determined with respect to the stage and thereby enable the control system 40 to adjust the position of the stage into alignment with a desired tip of the automated tool system 26.

By way of example, the system calibration function 54 is programmed to control the stage motion system 28 to move to a plate or other tray under the tool tip that has been positioned to its predefined reference location and aligned with a location. An ink or other transferrable medium (e.g., ink or other marker material), which is visible to the imaging system 20 can be applied to the tip of the tool. The indicia can be applied to the stage or an object disposed thereon by moving the tip carrying a marker material (e.g., ink or other marker material) into contact with the surface of the stage, for example. The position of the stage (e.g., in two- or three dimensional space) can be recorded. This stage carrying the applied indicia is then moved under the microscope until the applied marker is located and a new coordinate position of the stage (e.g., in two- or three dimensional space) is recorded. With these two pieces of information, the relative location of the tool reference position and the microscope optical centerline is known. This tip to optical offset information is used to calibrate the system to enable precise and reproducible positioning of the tool with respect to targets on a corresponding set of one or more well plates identified in the captured images. The tip to optical offset calibration can be performed for each set of plates or other apparatuses that are positioned on the stage.

In the addition to the system calibration 54 determining the tip to optical offset, such system calibration 54 can also ascertain a tip-to-tip spatial offset between a reference tip and one or more other tips that can replace the reference tip on the tool (e.g., a mandrel). As used herein, the reference tip can correspond to a given tip that is utilized initially to determine the tip to optical offset mentioned above and each other tip that is attached to the tool (e.g., a mandrel, such as a hollow body of a syringe tool apparatus) can be calibrated to determine a corresponding tip-to-tip spatial offset with respect to the same given reference tip.

The system 10 can include one or more sensors integrated into the stage 12 to provide tip position data representing a location of the tip with respect to each of the orthogonal (e.g., X,Y) axis of the stage 12. For example, the tool can be positioned at its predefined reference position (e.g., based on predetermined tool motion data 36 stored in memory), and the stage can move relative to the tip, while the tool is located at its predefined reference position, to identify the coordinates of the tip with respect to the axes of the stage based on the tip sensor data. As disclosed herein, the reference position of the tool can be any predefined repeatable position to which the tool can be accurately positioned. This can be repeated for a subsequent tip and the difference between the tip locations, as provided by the tip sensors, can define the tip-to-tip offset between the other tip and the reference tip. The system calibration 54 of the control system can in turn aggregate the tip-to-tip offset with the tip to optical spatial offset determined for the reference tip to enable accurate positioning of the stage 12 via the stage motion system 16 with respect to the new tip. Examples of such tip sensing and calibration functions are disclosed herein with respect to FIGS. 6-8.

In some examples, the automated tool system 26 can also include a tool function system 30 that is configured to activate an associated function of the tool for interacting with an identified target (e.g., one or more cells or cell colonies) based on tool action data 38. For the example, the tool comprises a syringe apparatus that includes a hollow body mandrel to which a tip is removably attached and that provides fluid communication to a fluid source. In such example, the tool function system 30 can activate the syringe for aspirating with the syringe by controlling the flow rate and volume of material that can be drawn into a tip of a tool containing an inner channel through which a controlled flow of fluid or medium can be implemented to aspirate or dispense.

Examples of variables that can be selectively controlled based on the image analysis 24 can include volume, flow rate, force, time and/or rate of change of pressure (e.g., positive or negative pressure), height of the tip relative to the object and/or stage 12 as well as pattern and movement of the tip relative to the stage 12, as well as combinations thereof. The relative motion between the tool tip and the stage can be controlled, for example, based on the tool motion system 28 along two or more of orthogonal axes. Alternatively or additionally, relative motion between the tool tip and the stage can be controlled based on the stage motion system 16 controlling position of the stage along two or more orthogonal axes. For example, the tool tip can be moved to a computed centroid of the target object and the tip can be positioned at a computed distance (e.g., along the Z axis) from the stage for aspiration or other interaction. The dimensions for a selected tip can be utilized as interactive protocol and process parameter to enable control of the tool subsystem and the tool and fluidics system, for example.

As a further example, the fluid flow parameters can be stored in memory, such as part of tool action data 38 that includes a library of interaction protocols. Each respective interaction protocol can include a series of "process steps" or actions, each having a defined set of "parameters" that characterize each step that is to be performed in a sequence or concurrently. The library of interaction protocols can includes predetermined schemes applicable based on the sensed data and image analysis. Additionally, the interaction protocols may include one or more user configurable schemes that can be generated in response to inputs via the user interface 18. As one example, a given aspiration scheme can be selected as part of a given interaction protocol based on the image data 22 (including derived from image analysis 24) and other data (e.g., sensor data 52, tool motion data 36, user input data and the like).

For example, a given interaction protocol may be selected from a library of one or more pre-programmed interaction protocol, which can vary with respect to variables associated with tool selection and tool aspiration controls. For example, the schemes can be programmed to vary based on, including but not limited to: tool selection, aspiration tool design and rotational orientation, pattern of movement, height during aspiration, flow rate, volume aspirated, pattern of directionality of flow or tool movement, as well as stage motion. The use of chelating agents or changes in plate or fluid temperature to reduce cell-cell adhesion or cell surface adhesion may also be used. The addition of chelating agents (e.g. ethylene glycol tetraacetic acid—EGTA; Ethylenediaminetetraacetic acid—EDTA), changes in plate or fluid temperature, or addition of other bioactive agents prior to aspiration may also be used to reduce cell-cell adhesion or cell surface adhesion. A given interaction protocol can be selected or modified based on object cell type (e.g., connective tissue progenitor cells, mesenchymal stem cells, endothelial cell, keratinocyte, neuron, induced pluripotent stem cells, or the like). The selected protocol may be updated or modified based on object features (e.g., size/area, size/cell number, thickness, density, distribution (e.g., uniform or dense center), substrate/surface features, extracellular matrix features or the like.

Data associated with the tool motion can be stored as part of the tool motion data 36. Similarly, data associated with the aspiration, including aspiration control parameters and aspiration scheme, can be stored in memory as part of the tool action data 38. The tool motion data 36 and the action data 38 further can provide feedback information during the process which can further be utilized to refine the variables and process parameters in a selected interaction protocol. The feedback can be derived from multiple acquired images (e.g., over a time interval) of areas that have the site of tool interaction or fluid flow intervention or aspiration. Basically, after a cell colony is located, the control system 40 activates corresponding process controls 42, 44, 46 and 48 to interact with the colony according to each sequence of steps in the selected interaction protocol. After the interaction, the sample containing the biological object is assessed using the automated imaging processing (e.g., image analysis 24) of acquired image data 22. Analysis of images before and after interaction can then be used to detect and measure the effect of the interaction and/or the combined effect of a sequence of interactions. These data can then be used, based on predetermined criteria, to proceed to a next phase in a series of steps in an automated interaction protocol. Alternatively, direct visual feedback information can be provided derived based on a comparison between image data before and after an interaction or series of interactions. From this visual feedback information compensations can be manually entered in to the motion algorithm for a subsequent interaction with the objects on the stage.

Additionally, during the process, image data 22 can be acquired continuously or intermittently. For example, actions associated with the movement of the syringe can occur and corresponding image data can be acquired. The control system 40 can employ the acquired image data to dynamically update and adjust the position parameters for the tool based on the analysis of the image data 22. As a further example, the distribution of pixels of voxels corresponding to the image data can be updated dynamically during the process of tool motion and/or aspiration based on the acquired image data to enable corresponding adjustments (e.g., in substantially real time) by the tool motion system and the tool function system 30.

The control system 40 further can access the data that is provided by one or more of the respective subsystems, including the image data 22, stage data 17, tool motion data 36 and tool action data 38. The system 10 can also include one or more environmental sensors 50 that can be configured to provide corresponding sensor data 52. Environmental sensors can include sensors for providing sensor data indicative of temperature, environmental pressure in the handling chamber, humidity and the like. The control system 40 thus can also receive the sensor data 52 for implementing corresponding control of the system 10.

For example, the imaging control 42 can control various parameters of the imaging system 20, including to control which optics are employed as well as activation of a light source and optical filters utilized during image acquisition. The imaging control 42 also controls activation of the camera acquires images (e.g., at automatic intervals and/or in response to user input via user interface 18). The imaging control 42 further enables the image analysis 24 to analyze values of the pixels or voxels in the corresponding distribution of pixels or voxels provided by the image data 22.

As an example, the image analysis 24 can determine one or more features of an object of interest based on the values of pixels or voxels. Then based on the determined features, the tool motion control 46, stage motion control 44 and/or function control 48 can provide corresponding control signals to the automated fluidic tool system 26 to control positioning of the tool then implement desired interaction with identified objects.

As another example, the tool function control 48 can be configured to control one or more of the volumes of fluid to be aspirated as well as the flow rate during aspiration. For instance, the function control 48 can control the positive and negative pressure applied across the tip can with respect to flow rate and direction, thereby controlling the flow rate and volume of material passing through the tip of an automated syringe apparatus that is implemented as the automated tool system 26. In some examples, the function control 48 can control the flow rate up to about 500 μl/second or greater.

Additionally or alternatively, as part of the process, the tool motion control 46 and/or the stage motion control 44 can be configured to adjust a height of a tool tip relative to the surface containing the object of interest and the medium and/or the articulating pattern of the needle during aspiration, such as based on one or more of the acquired data 17, 22, 36, 38 and 52. The interoperation between the subsystems is driven mainly from the optical information obtained from image data 22 and the image metadata 23. The location and size of the cells are computed (e.g., in system coordinates), such as disclosed herein, corresponding motion and aspiration processes are executed using one of the interaction protocols.

As yet a further example, the tip (e.g., needle of the syringe) can be replaced or removed in an automated manner. For instance, the tool system can include a replaceable tip, which can be automatically selected from a plurality of different available tip designs. A selected tip can be configured to attach a distal end of the tool via a mating interface. Various types of interfaces (e.g., friction fitting, threaded interface or the like) can be implemented. As one example, the interface can be a wedge shaped press fit on the tool that may be applied by pressing the fitting at the free distal end of the tool (e.g., a mandrel) into the tip. The tool system 26 controls the pressure during tip attachment, such as between two levels—high enough to make a solid interface by not too high that it damages the tip. The tool of the tool system 26 can include an integrated force sensor in the bracket that holds the tip. The force sensor can provide force information (e.g., as part of tool action data 38), which is monitored by the control system 40. The control system 40 can providing the force information back to the tool motion system 28 to control the force in the Z-direction while the tip is being applied to the tool holder. The tool system 26 can also include a spring loaded holder that helps ensure proper force is applied during loading.

Different tip designs can be selected (e.g., by control system or in response to a user input) depending on the interaction that is needed and the medium from which the cells and/or colonies and nearby media are to be extracted. Different media can be categorized differently, such as a fluid, viscous fluid, semi-solid, gel, hydrogel or the like, and a tip can be selected according to the categorization of the medium that is present. The category of medium can further be a process parameter used to control aspiration for a given interaction protocol.

Additionally, the tools can be designed for single use and be disposed of in a receptacle after use. For a replaceable tip design, removal of a tip may be implemented by a "shucking" device. For example, the shucking device can be implemented as a keyhole structure (e.g., a large diameter hole intersected by a smaller diameter slot) located a predefined tool coordinates. The loaded tool is lowered into the large hole and once below inside the key hole, the tool is moved laterally into the smaller slot area. The tool is then moved up (e.g., in the Z direction) such that the tip catches the edge of the key hole slot and is removed from the tool. The key hole can be located such that the tip will drop into a waste receptacle. In other examples, another means (e.g., gripping device, such as a clamp or the like) can be used to remove the tip from the tool body.

In other examples, the tip may be reusable. For instance, the control system 40 can be configured to implement automated washing and/or sterilization of the tool tip and reservoir between successive interactions with a given tool tip that may be integral with the tool (e.g., fixed as not intended to be replaceable). Examples of tools that may be fixed or otherwise not replaced may include a cutting tool, a scraping tool, a stamping tool or a stirring tool. In other examples, the tool system 26 can include a plurality of different tools that can be utilized sequentially or concurrently to interact with selected objects, including aspiration of objects into respective tips. Some tips further can be multi-purpose tips to perform more than one of the interaction functions disclosed herein.

As a further example, an interaction can include pretreatment applied via one or more tools, such as to prepare one or more target objects for subsequent interaction. Examples of pre-treatment can include: removal of non-adherent cells or material (e.g. change of medium overlying the object prior to interaction); removal of cells or material from the object prior to interaction (e.g. blow off cells or material loosely adherent to the object); remove adjacent cells or material that may complicate or hinder the effectiveness of the interaction with the object; application of pretreatment chemical or biophysical methods to change the interaction of the object or object components (cells) with each other or the underlying surface such as Examples of pre-treatment chemical or biophysical methods may include medium agitation (e.g. Shaking or stirring), temperature Change within the chamber, media Change (e.g., removing Ca or Mg) and/or enzymatic digestion and quenching (e.g, with associated time controls).

Additional controls can also be implemented by the stage motion control 42 and/or the tool motion control 46 for controlling the interaction of the object 14 located on the stage 12. As disclosed herein, for example, the control system 40 can be programmed to determine the distance of the object of interest that is located in the medium on the stage 12 relative to at least one other object located in the same medium based on the distribution of pixels or voxels provided by the image data 22. For instance, the distance between objects can be based on the image analysis identifying objects and computing centroids for each object and then computing a corresponding distance between the respective centroids. The distance can be an absolute distance or it can be a distance computed as a number of pixels or voxels along a line between respective centroids, for example. In other examples, the position of the object of interest can be computed in a desired spatial coordinate system to facilitate interaction. The control system 40 can be further programmed to control the type of interaction or exclude interaction with the given object based on the determined distance and other conditions determined based on the image data and other process parameters. For instance, if an object is too close to another object the determination can be made to exclude aspirating the cells at such area.

In the event that an object of interest is in proximity to other objects or materials of non-interest, means can be employed to separate the object of interest from non-interest prior to direct interaction with the object of interest by means of physical interaction using an automated aspirating or non-aspirating tool to dislodge or remove adjacent or adherent objects or materials. For example, the tool action control can be programmed to direct a controlled flow of fluid over the top of the object to displace less adherent cells or materials. Alternatively, an aspirating or non-aspirating tool may be manipulated across the surface to dislodge and remove objects of non-interest, leaving an object of interest effectively isolated for use or making it more accessible for precise controlled interaction at a subsequent step in the current interaction protocol.

The imaging analysis 24 can also be programmed to divide the distribution of pixels detected from an image into discrete spatial regions and/or form a montage of plurality of discrete images, such as disclosed in Appendix A. Each spatial region is assigned its own respective distribution of pixels or voxels therein. The distribution of pixels or voxels for each respective spatial region can be utilized by the control system 40 to control the automated tool (e.g., syringe) 26 for performing selective aspiration on based on the distribution of pixels or voxels within the given respected spatial region. Additionally, the tool function control 48 can be further programmed to determine an interaction protocol that is selected for each discrete spatial region based on the corresponding distribution of pixels or voxels for each such region. In this way the tool function control 48 can set a corresponding interaction protocol (e.g., for aspiration and/or another form of interaction), such as for setting the processing parameters and controlling aspiration of each object of interest that is located in each respective spatial region.

As mentioned above, the imaging control 42 can be programmed to continue to acquire images either during interaction/aspiration or in between discrete phases of the interaction process. For example, the imaging system 20 can update the image data to reflect changes in the distribution of pixels or voxels for each of the respective spatial regions within an image field of view in response to corresponding interactions (e.g., aspirations) with the objects of interest. In yet another example, the imaging system can update the spatial region in which the object resides and the immediate adjacent neighboring regions to the region containing the object of interest. The image analysis function 24 can further divide each of the images into corresponding discrete spatial regions based on location metadata that is embedded in the image data 22. Such spatial regions may be the same or vary throughout the interaction process. The image analysis 24 further can continue to analyze the distribution of pixels or voxels within each spatial region to provide updated dynamically varying imaging data reflecting changes in the distribution of pixels during such interactions or in between each of a sequence of interactions. As a result, the tool function control 48 and tool motion control 46 can dynamically adjust the process parameters associated with the automated tool 26 for each spatial region containing an object of interest based on the changing imaging data that has been provided by the image analysis 24.

In view of the foregoing it is to be understood and appreciated that the image data 22 that is acquired by the imaging system 20 and the analyzed image data from the image analysis 24 can be converted into process parameters to control interaction with one or more selected object of interest. For example, the control system 40, including the tool motion control 46 and the tool function control 48, can be programmed to compute processing parameters for an interaction protocol based on the distribution of pixels or voxels for an object of interest or a feature of an object of interest determined from the image analysis 24 for the pixels or voxels. Other information, such as sensor data and the category of medium, can also be used in determining the interaction protocol's processing parameters.

By way of further example, each object of interest, such as a cell or a group of cells (e.g., cell colony) can include one or more morphological features that can be readily determined by the imaging analysis 24 according to the values of pixels or voxels for each object of interest and the distribution of pixels or voxels for the object of interest. That is, in addition to the distribution of pixels or voxels, corresponding morphological features corresponding to the values of the respective pixels or voxels can be combined for further characterization. The morphological features can include, for example, cell morphology or morphology of a colony of cells, such as disclosed in the above-incorporated U.S. Pat. No. 8,068,670.

The tool motion control 46 further can be programmed to control the motion of a tool relative to the stage or other substrate in which the object of interest 14 is located. As mentioned above, the tool motion control 46 can control motion and position of the tool in three-dimensional space (e.g., via respective linear motors or actuators) based on the distribution of pixels or voxels for a given object of interest provided in the image data 22. Based on the established parameters for positioning the tool in contact with or at a predetermined distance separated from the object of interest, the tool function control 48 can in turn control the flow of the object of interest into an aspiration tool, again, based on the distribution of pixels and based on the analysis of the values of pixels or voxels for the given object of interest to be aspirated.

There can be any number of one or more aspiration schemes defined by respective interaction protocols that can be stored in memory and selected for use in facilitating isolation and harvesting of cells. The aspiration scheme may be selected among the options in the protocol library, such as based on the imaging features of the object of interest (e.g., size, density, shape, morphology, expression of selected surface markers, or the like). For example, the tool function control 48 can be programmed to select an interaction protocol from the library of interaction protocols to implement an aspiration scheme based on the analysis of the image data acquired for the objects located on the stage and in response to a user input, such as can be provided the user interface 18. For example, the user input can be utilized to specify a desired type of interaction or type of aspiration as well as one or more parameters associated with such operations. Additionally or alternatively, the user input can establish a minimum colony size and define a type and material properties of the media in which the objects are being cultured. The selected aspiration scheme and the analysis of the image data can be stored into a knowledge base to further document the application of the aspiration scheme for harvesting the object of interest. The set of process parameters associated with each interaction can also be stored in memory for subsequent analysis and evaluation. In this way, process parameters can be further adjusted for subsequent harvesting based on the evaluation of the effectiveness of the scheme and the parameters utilized to harvest the object of interest.

As a further example, one or more parameters, such as tip distance from the object, flow rates, pressures and positioning of the tool relative to the object of interest can be evaluated relative to the results of the aspiration and harvesting process to determine the effectiveness of such parameters during aspiration. Moreover, the user input can further set a type of interaction, such as sample, move, remove, or kill an object of interest, depending upon whether it is determined that the object of interest is to be retained, transferred or removed from the medium.

In some examples, a given colony or group of cells may require multiple interactions or aspiration phases to displace unwanted cells or objects and/or to retain desired cells in the medium or capture the desired cells into the inner chamber of an aspiration tool for transfer. Accordingly, between each of the sequences of aspiration phases, calibration updates can be implemented dynamically to help optimize a next aspiration phase for the selected interaction protocol. For example, flow rates and distances can be adjusted, position of a needle can be readjusted and different flow rates can be utilized based on the distribution of pixels and voxels detected between each aspiration phase. As an example, the distribution of pixels before and/or after an aspiration sequence can be compared or correlated to ascertain process parameters for the next phase of aspiration.

The image analysis 24 further can be programmed to determine an object profile for each object of interest based on the analysis of the distribution of pixels or voxels for the object of interest. As an example, an object profile may be compiled from an integrated series of algorithm steps, each applying a specific operation or range of specific variables including specific steps of imaging, image processing (e.g., thresholds, filters, maps, masks, segmentation, correction) steps. These may develop an object list that can be further refined by specific inclusion and exclusion testing criteria based on size, morphology, density, brightness, texture, gradients, proximity, shape, pattern and the like. Individual (discrete) profiles for detection and classification of specific object types may differ by one or more steps or parameter range or threshold settings. The process parameters for controlling interaction such as aspiration with each object of interest thus can be selectively adjusted based on the object profile that has been determined. As an example, the object profile can be assigned to each discrete spatial region occupied by corresponding objects of interest and the object profile further can be updated dynamically based on the distribution of pixels or voxels being acquired for each phase of the process.

After the objects of interest have been harvested into the inner passage of a tip (e.g., needle) of an aspiration tool, the stage motion control 44 and tool function system 28 can cooperate to move the selected objects from the needle to a subsequent destination, which can reside on the stage 12 or another location within the system 10. For example, if the objects or cells that have been aspirated into the needle for deletion, the needle can be moved so that can be discarded to an appropriate disposal site. In other examples, the cells can be transferred to a new site, such as being re-plated into a medium for additional growth and subsequent harvesting.

As mentioned above, the location of a tip of tool, which may be integral with tool or be replaceable, is to be known in three directions, X-Y and Z. To enable accurate control for interactions with objects on the stage, these locations are calibrated to relate each motion system that is involved in the interaction. Additional examples of calibration and interaction between a tip of a tool and one more objects on a stage will be better appreciated with respect to the example of the system configuration depicted in FIGS. 2-10. In the examples of FIGS. 2-10 identical reference numbers refer to the same components and additional reference can be made to the system 10 of FIG. 1 for integrated controls and operations.

Figure 2:
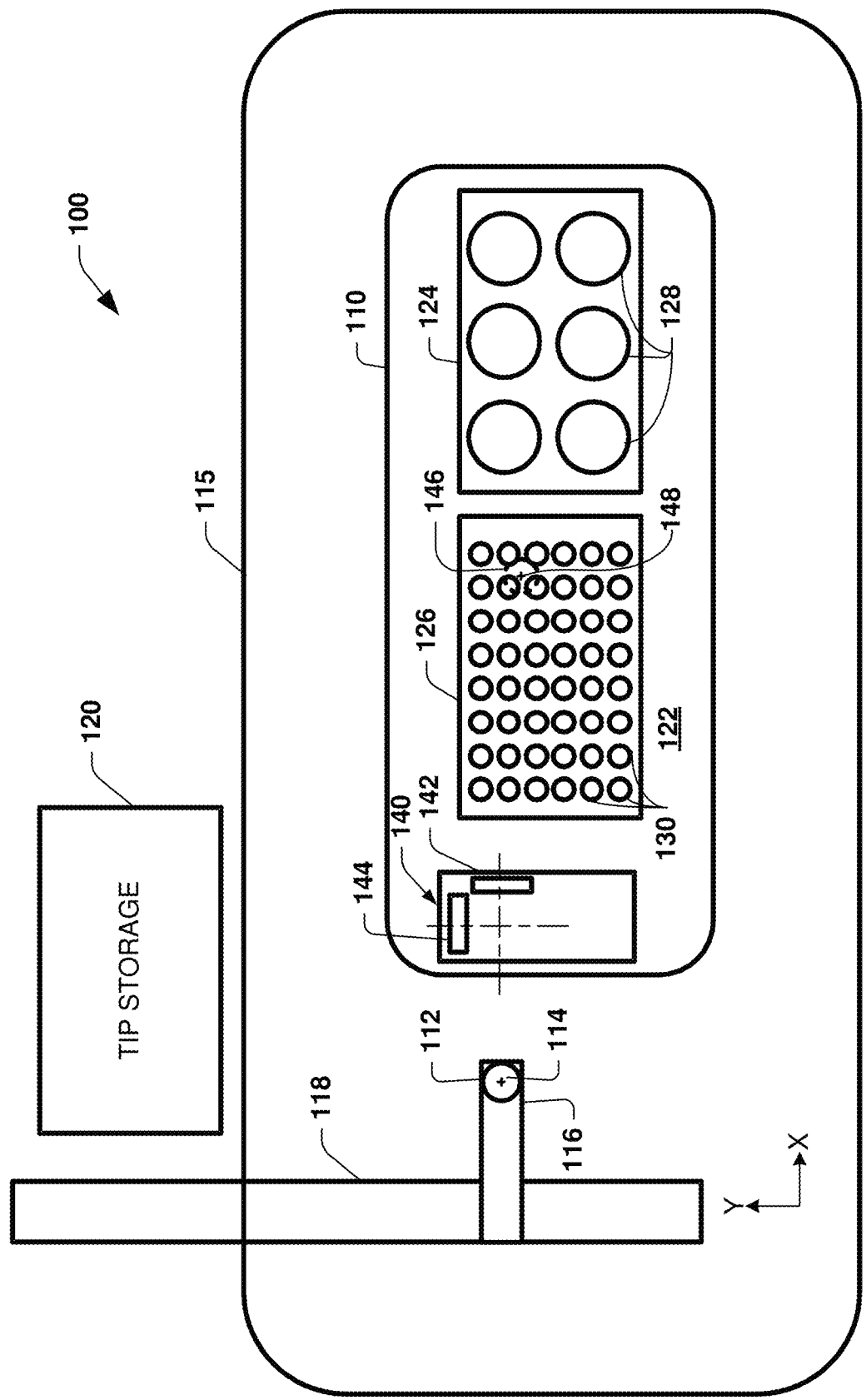
FIG. 2 depicts a plan view of an example of part of a system showing spatial relationships between a movable tip and a stage.

In the example of FIG. 2, the system 100 includes a stage 110 that is movable along at least two orthogonal axes, identified as X and Y. The stage 110 can be movable relative to one or more tools 112 that can include a tip that extends axially from the tool to terminate in a corresponding distal end of such tip. The tool 112 can be controlled to move the tip axially in a direction that is orthogonal to a plane defined by the X and Y axes of the stage, in the Z direction. The tip includes a longitudinal central axis, identified at 114. In addition to movement of the stage 110 along the X and Y axes with respect to a system frame or housing, schematically indicated at 115, the tool 112 can also move along the Y axis via operation of the corresponding motors to move tool holder arm 116 with respect to mounting arm 118. The tool can also be moveable in the Z direction via control of a linear actuator. For example, the Z-axis motor of the tool 112 can be implemented as mechanical actuator (e.g., a ball-screw servo motor, a lead-screw motor, etc.), a linear motor, a segmented spindle motor, a moving coil motor (e.g., rotary, linear or rotary-linear), or the like.

As a further example, the tool holder arm 116 can be movable in the Y-direction via actuation of a corresponding linear motor or other actuator. The tool 112 can also be moveable in the Z-direction with respect to the stage 112 via actuation of the corresponding motor (e.g., a linear actuator). Similarly, the stage 110 can be movable in the X direction in response to actuation of the corresponding linear motor that is attached the stage 110 and corresponding base (e.g., frame or housing) of the system 100, and in the Y direction in response to an actuation of another linear motor fixed to the stage 110 and to the base of the system 100. The stage 110 includes a surface 122 on which various components can be located.

As one example, the tool 112 can be implemented to include a hollow body that is fluidly connected to a source of fluid which can be activated to add or remove fluid through the hollow body and a corresponding tip that is attached and extends from to the hollow body. For instance, a tip can be removably attached to the hollow body, as mentioned above such as by a friction fitting between an interior sidewall of the tip and the outer sidewall of the mandrel of the tool body. Other types of attachments, such as threaded fasteners and fittings, may also be utilized to secure the tip with respect to the tool 112. Since, in some examples, the tip is removable with respect to the tool, each tip that is attached to the tool can result in spatial variation of the distal end of the tip in three-dimensional space, including in X and Y coordinates of the stage 110 as well as in a Z direction that is orthogonal to the surface of the stage. Accordingly, the system 100 employs calibration to resolve the position of the tip spatially.

In example of FIG. 2, two well plates 124 and 126 are positioned spaced apart from each other on the surface 122 of the stage. While the example of FIG. 2 demonstrates two well plates 124 and 126 it is understood that the stage can accommodate any number of one or more than one plates according to application requirements. Each of the plates 124 and 126 can include one or more wells into which cells can be received and removed via the one or more tools (e.g., syringe tool apparatuses) 112 implemented within the system 100. As disclosed herein, the tools (e.g., a cutting tool, a scraping tool, a stamping tool or a stirring tool) can also perform other types of interactions with the cells or other objects or media that may be disposed in the wells 128 and 130 on each of the respective plates 124 and 126. Additionally, the enclosure 115 is designed to maintain environmental conditions within the enclosure to facilitate growth and cleanliness of cells and other objects that may be placed onto the well plates 124 and 126.

In some examples, the system 100 can also include a tip sensing system 140, which may be integrated into the stage 110 and configure to interact with the tip of one or more tools. The tip sensing system 140 can include hardware that includes sensors 142 and 144 for detecting a position of a tip of the tool 112 in each of the X and Y axes of the stage 110. The sensor 142 can be configured to detect the Y position of the tip of the tool 112 and the sensor 144 can be configured to detect the X position of the tip of the tool.

As a further example, the tip sensor 140 can be a non-contact sensor, such as using optical interrupter devices oriented 90 degrees from each other in the direction of the X- and Y axis. When the tip sensor 140 is utilized to detect the X and Y positions of the tip, the tool 112 can be positioned at a predefined X and Y position with respect to the arms 116 and 118 relative to the housing 115 of the system 100. This predefined location (e.g., referred to herein as the tip reference position) can be identified and stored in memory as to be reproducible for each subsequent tip that may be attached to the tool 112. As another example, the tip sensor 140 could be implemented using an X-Y laser gauge fixed with respect to the stage, which outputs not only the position of the tip with respect to the stage coordinates, but also the diameter of the tip.

As disclosed herein, the imaging system can include a camera that provides an object field of view 146 at a corresponding location that can remain fixed with respect to the housing 115 of the system 100. The field of view 146 can include an optical axis 148, demonstrated at the center of the field of view 146. Thus, in order to capture an image of a desired location on the surface of the stage 110, stage motion system (motion system 16 of FIG. 1) can selectively adjust the position of the stage 110 in the X and/or Y axes so that the field of view 146 contains the desired object or other target of interest such as located in a corresponding well 128 or 130. The size and resolution associated with the field of view 146 can be selected by configuring optics 58 of the corresponding imaging system 20, as disclosed herein, automatically or in response to a user input.

Figure 3:
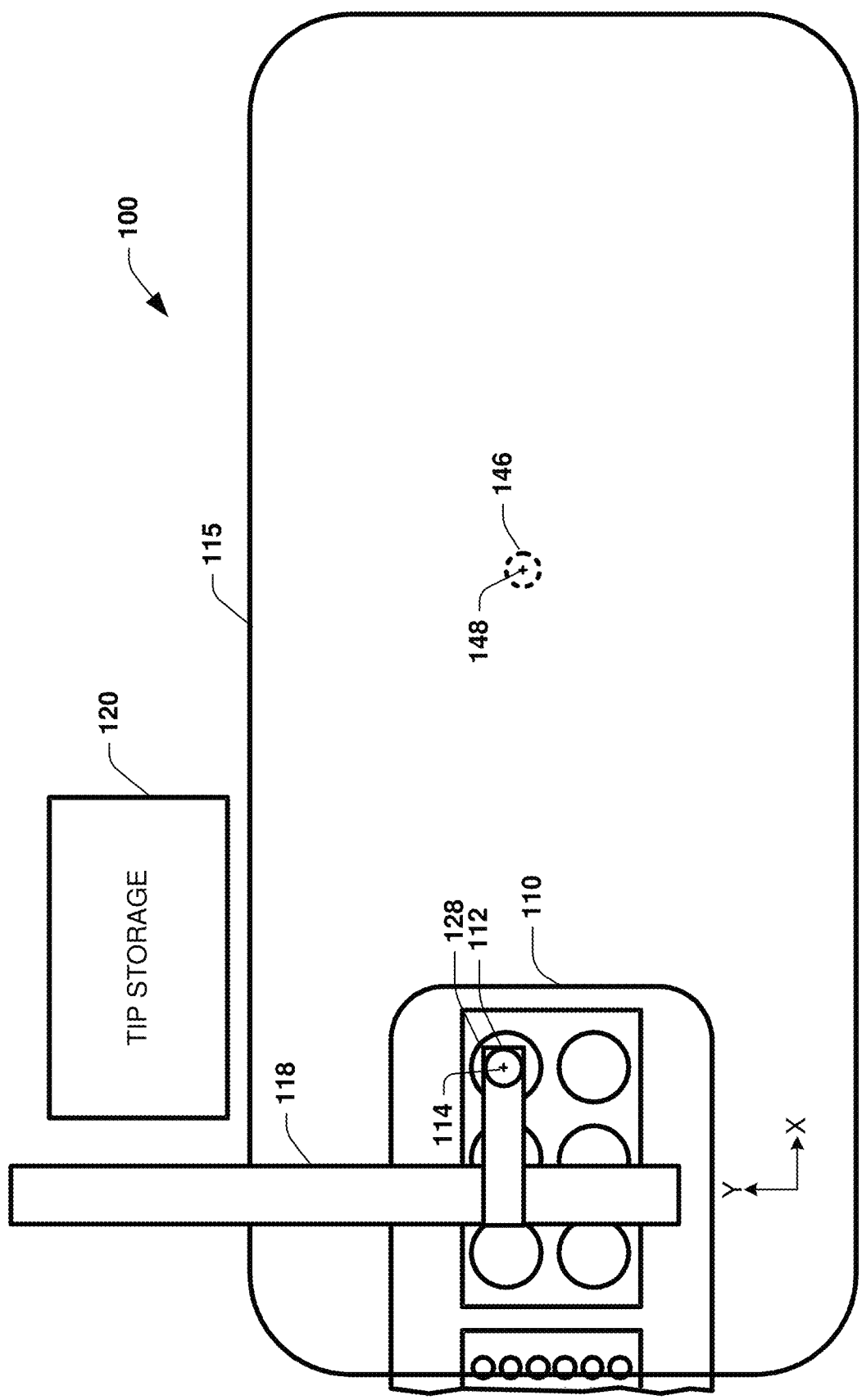
FIG. 3 depicts the system of FIG. 2 with the stage in a position for part of a calibration process.

FIG. 3 depicts an example where the stage 110 has been moved to a first position in which the tip 114 can be moved into contact with a location at the surface of the stage such as in a corresponding well. The particular location at which a reference tip contacts the stage can be arbitrary or predefined. The tool 112 can be moved along the Z axis 114 in the direction of the stage 110 until the tip contacts the stage or an object located on the stage such as the well or medium residing in the well. In response to engagement between the tip and contact site on the stage, a fiducial marker can be transferred onto the contact site. The marker can include ink or any other marker material that can be visually differentiated from the surroundings on the surface as to be detected by the imaging system. For example, the ink can be applied to the distal end of the tip prior to moving the tip into contact with the stage 110.

By way of example, the ink can be applied to the end of the reference tip. The distal end of the tip can be moved to contact an empty sample tray at a known empty location. For instance, the tool motion system can control the tip to contact the tray at a plurality of different X-Y location by moving the tip along its Z axis to stamp the tray with the ink that is on the end of the tip, thereby creating a fiducial mark (e.g., a circle) on the sample tray. After the fiducial mark (or a plurality of markers) has been transferred to the surface of the stage 110, stage motion system is activated to adjust the position of the stage 110 so that the fiducial marker is within the field of view 146 of the imaging device (e.g., microscope), such as demonstrated in FIG. 4.

Figure 4:
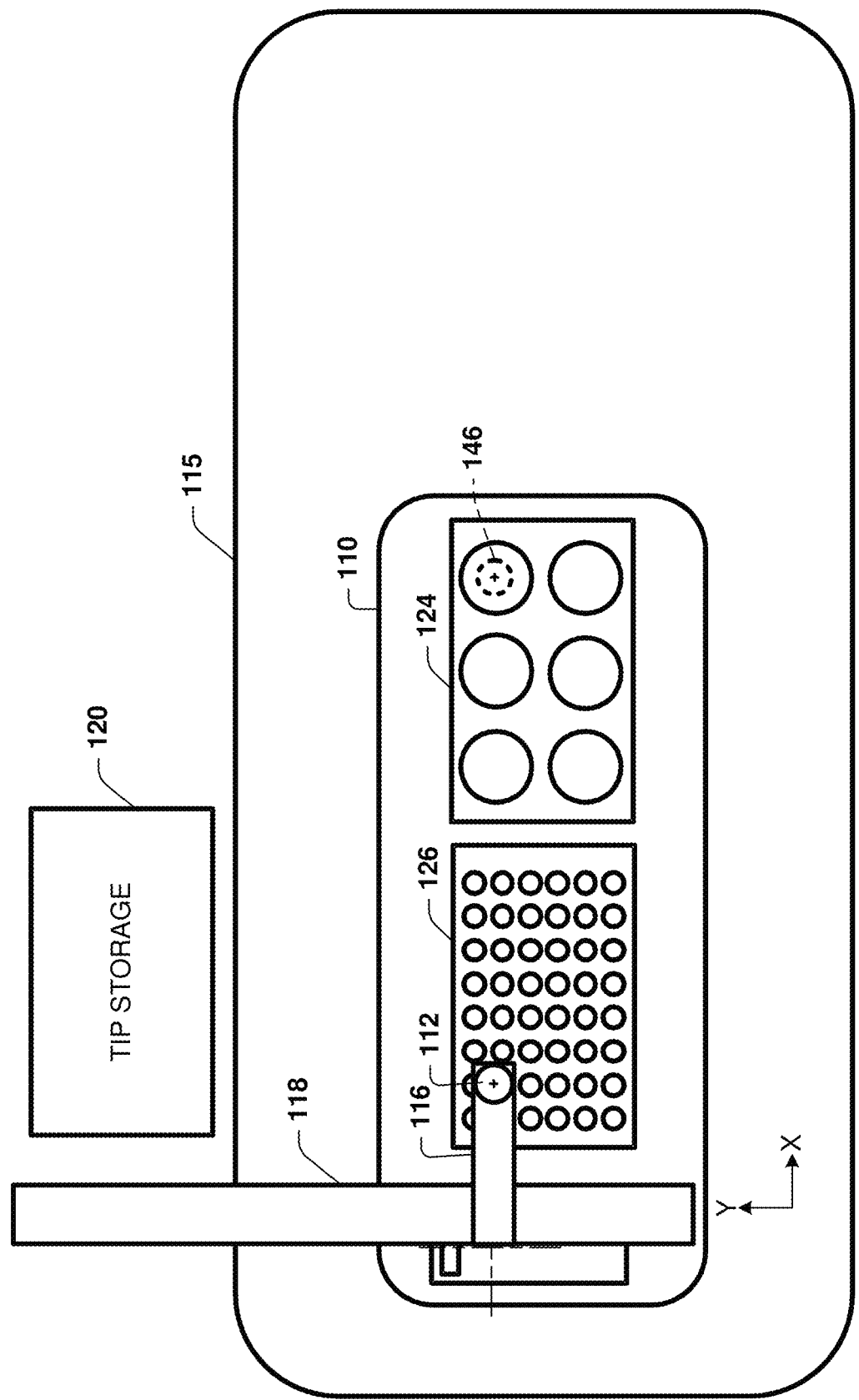
FIG. 4 depicts the system of FIG. 2 showing the stage in another location associated with the calibration process.

In some examples, the stage may be moved in response to user inputs (e.g., in the X and Y directions to position the fiducial marker within the optical field of view 146). In other examples, an automated method can be employed to adjust the position of the stage 110 with respect to the object field of view into the fiducial marker resides within the objects field of view. As yet another example, a combination of user inputs and automated detection can be utilized to adjust the positioning of the stage with respect to the optical field of view 146. For example, the stage position can be adjusted to place the fiducial marker along with the optical axis 148. Once the fiducial marker is located at the desired position within the object field of view 146, as shown in FIG. 4, the coordinates of the stage 110 can be stored in memory.

The system calibration function (e.g., function 54) of the control system can in turn calculate a difference between coordinates of the stage (e.g., X-Y coordinates) when the fiduciary marker was applied by the tip of the tool and the coordinates of the stage when the image was captured that contains the representation of the fiduciary marker within the objects field of view 146. The difference between the spatial coordinates of the stage at the respective positions for each fiducial marker determines an optical offset between the tip position (corresponding to the reference tip position) and the optical access. The positions of the stage can be determined from outputs of X and Y linear encoders that are associated with the respective linear actuators utilized to move the stage along each of its X and Y axes.

By way of example, the fiduciary marker can correspond to an ink dot having a diameter that is approximately 700 micrometers or less and the coordinates of such fiduciary marker can be determined according to a pixel or to a centroid of a group of pixels that contain the fiduciary marker from the image that was captured from the field of view containing the fiduciary marker. If the centroid or individual pixel for the fiduciary marker is not aligned with the optical axis, the image metadata (metadata 23 of FIG. 1) that specifies the resolution of the image can be employed to ascertain its spatial position of the pixel or centroid of pixels.

The spatial offset that is determined can be utilized to reproducibly to move the tip relative to a desired target that is identified within a field of view of a given image, such as to perform a desired interaction at the target object location. As disclosed herein, examples of some interactions that can be performed with respect to objects on the well plates 124 or 126 can include cutting material on the tray, scraping material on the tray, stamping material on the tray, stirring a medium on the tray or aspirating (e.g., picking) objects from the tray and/or transferring objects to one or more destinations.

For examples where the tip is a removable tip, such that it can be removed from the tool and replaced with another tip, the control system can perform additional calibration to ascertain a tip-to-tip spatial offset for each new tip that is used. In the following examples, it is presumed that the set of images stored as image data correspond to the same sets of plates 124 and 126 that are positioned at the same locations on the stage 110. In this way the calibration and any interactions are performed with the respect to a common set of images.

Figure 5:
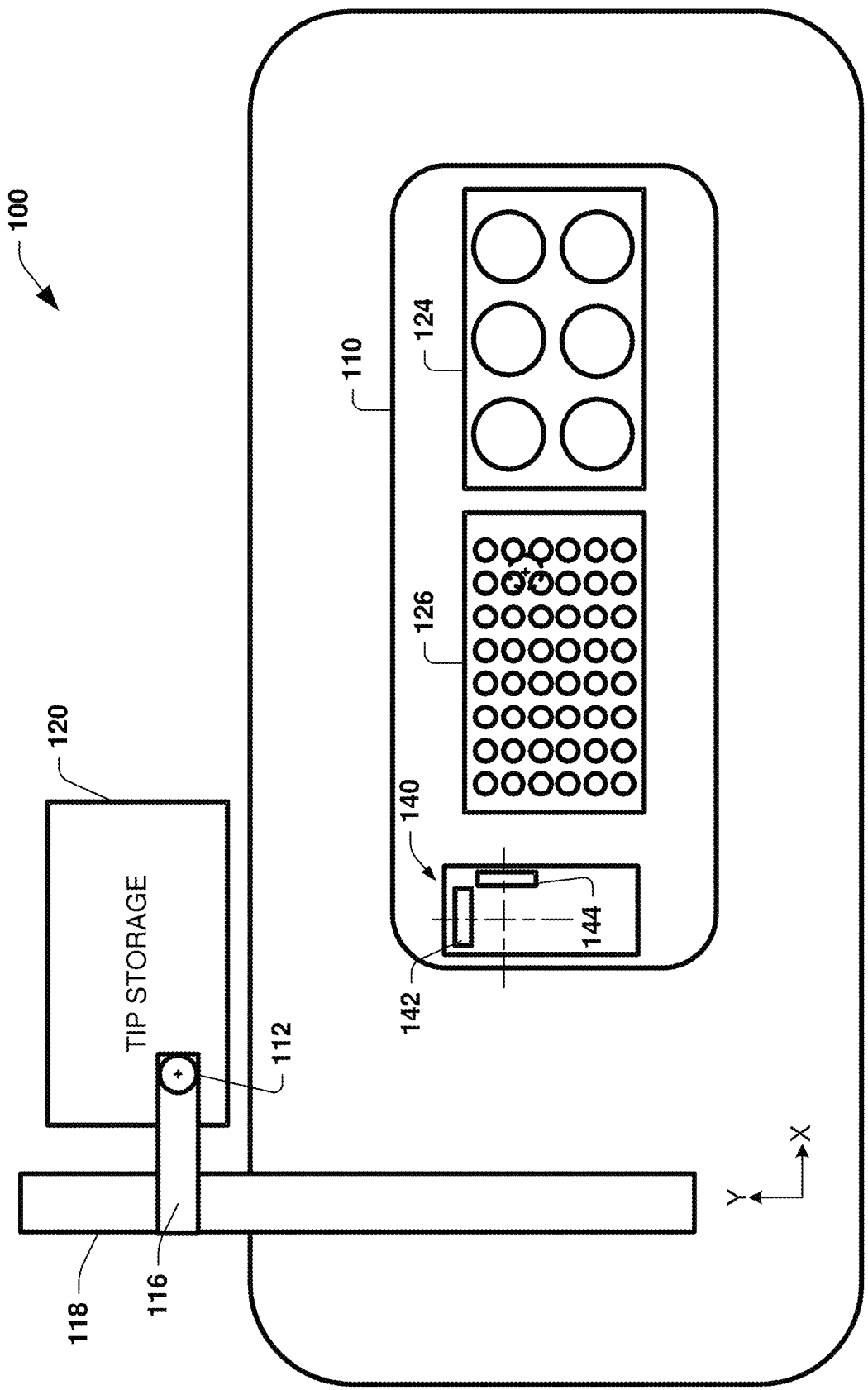
FIG. 5 depicts the system of FIG. 2 with the tool arm moved to a location for receiving a new tip.

As shown in FIG. 5, for example, a new tip can be placed onto the tool (e.g., mandrel) from tip storage 1202, such as after the previous tip (e.g., the reference tip or another tip) has been removed from the tool, such as disclosed herein. Once the new tip has been placed on the body of the tool, such as by automatic placement from the tip storage 120, the tip sensor 140 is activated to ascertain the location of the tip in X and Y coordinates for the stage. Such tip coordinates are determined for each tip used, including the reference tip. The tip-to-tip offset can be calculated as the difference between the tip coordinates of the reference tip and each other tip.

Figure 6:
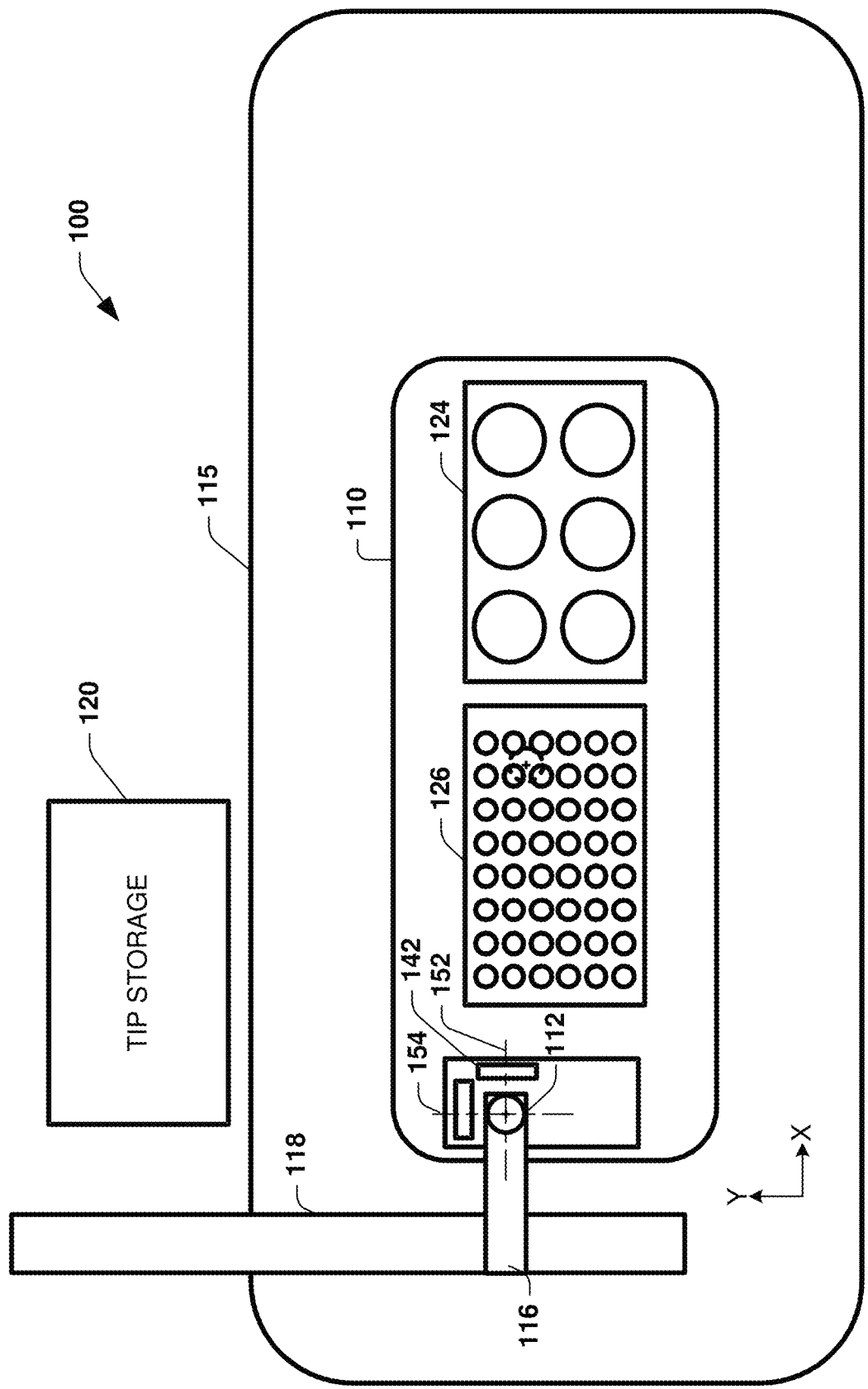
FIG. 6 depicts an example of the system of FIG. 2 demonstrating part of a tip sensing process.
Figure 7:
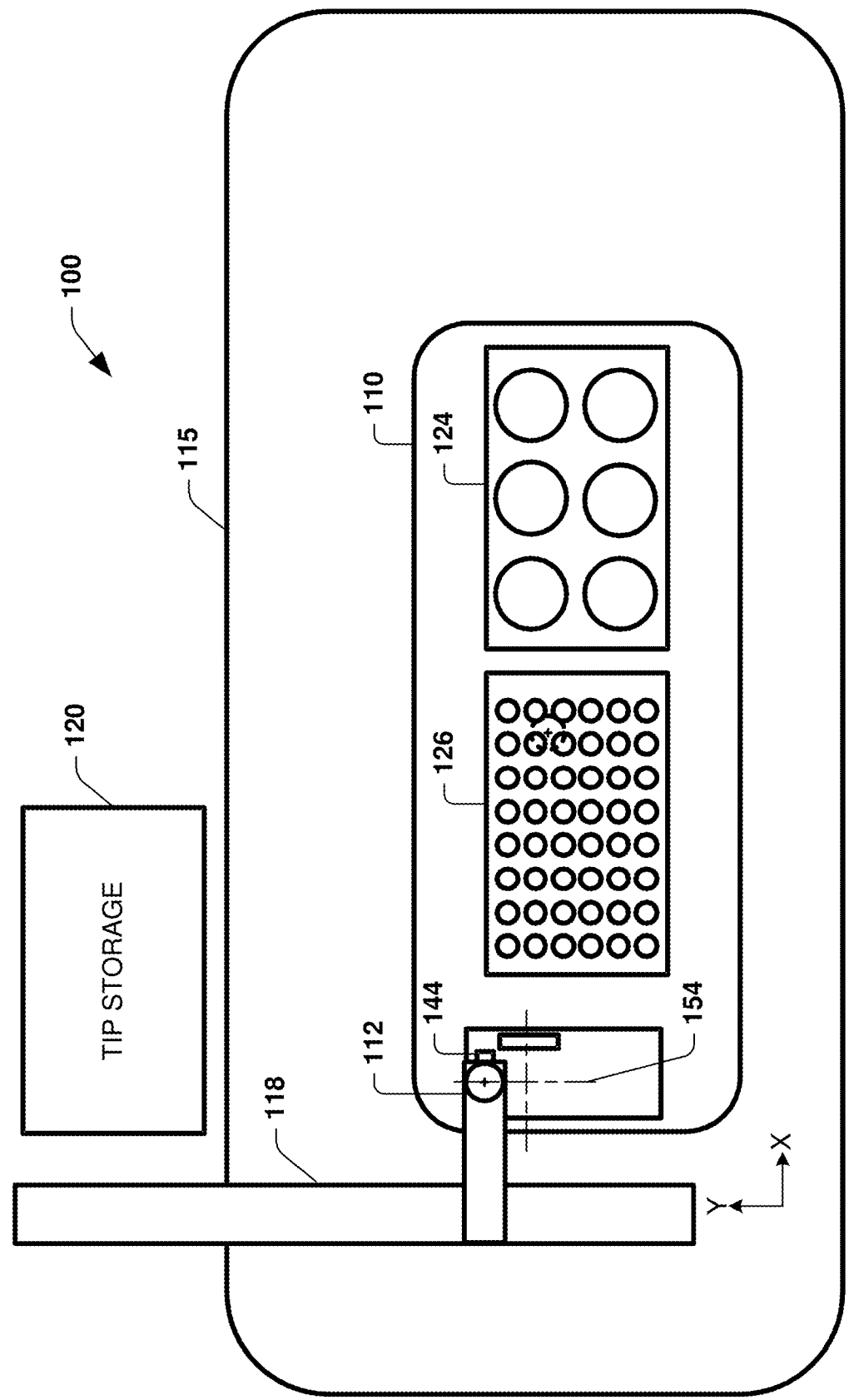
FIG. 7 depicts an example of the system of FIG. 2 demonstrating another part of the tip sensing process of FIG. 6.

For example, as shown in FIG. 6, the tool 112 can be repositioned back at the reference tip position, and the stage 110 can be moved in the X direction so that the Y coordinate for the tip of the stage can be identified by the sensor 142, as indicated by axis 152. Similarly, as shown in FIG. 6, the stage can be moved in the Y direction so that an X coordinate for the distal end of the tip is identified by the sensor 144, as demonstrated by axis 154. The intersection between the axes 152 and 154, as determined from sensors 142 and 144, corresponds to the tip position (X, Y coordinates) for a given tip. Based upon the tip coordinates for the reference tip and each other tip, a corresponding tip offset can be determined as the difference between the tip coordinates of the reference tip and each respective other tip.

The corresponding tip offset for a given tip can in turn be applied to the spatial offset determined for the reference tip (see, e.g., FIGS. 3 and 4) to provide the new optical offset. For instance, the X optical offset can be computed as the sum of the X coordinate for the optical offset and the X value of the tip offset, and the Y optical offset for such given tip can be the sum of the Y coordinate for the reference optical offset and the tip offset in the Y direction. The new optical offset is utilized by the control system 40 for controlling the stage motion system for positioning the distal end of the new given tip at a desired target location identified in a corresponding captured image. As a result interactions between the tip and objects on the stage can be implemented with a high degree of accuracy and reproducibility. For example, the precision of the X-Y tip sensor 140 is can be about +/−5 microns or better.

Figure 8:
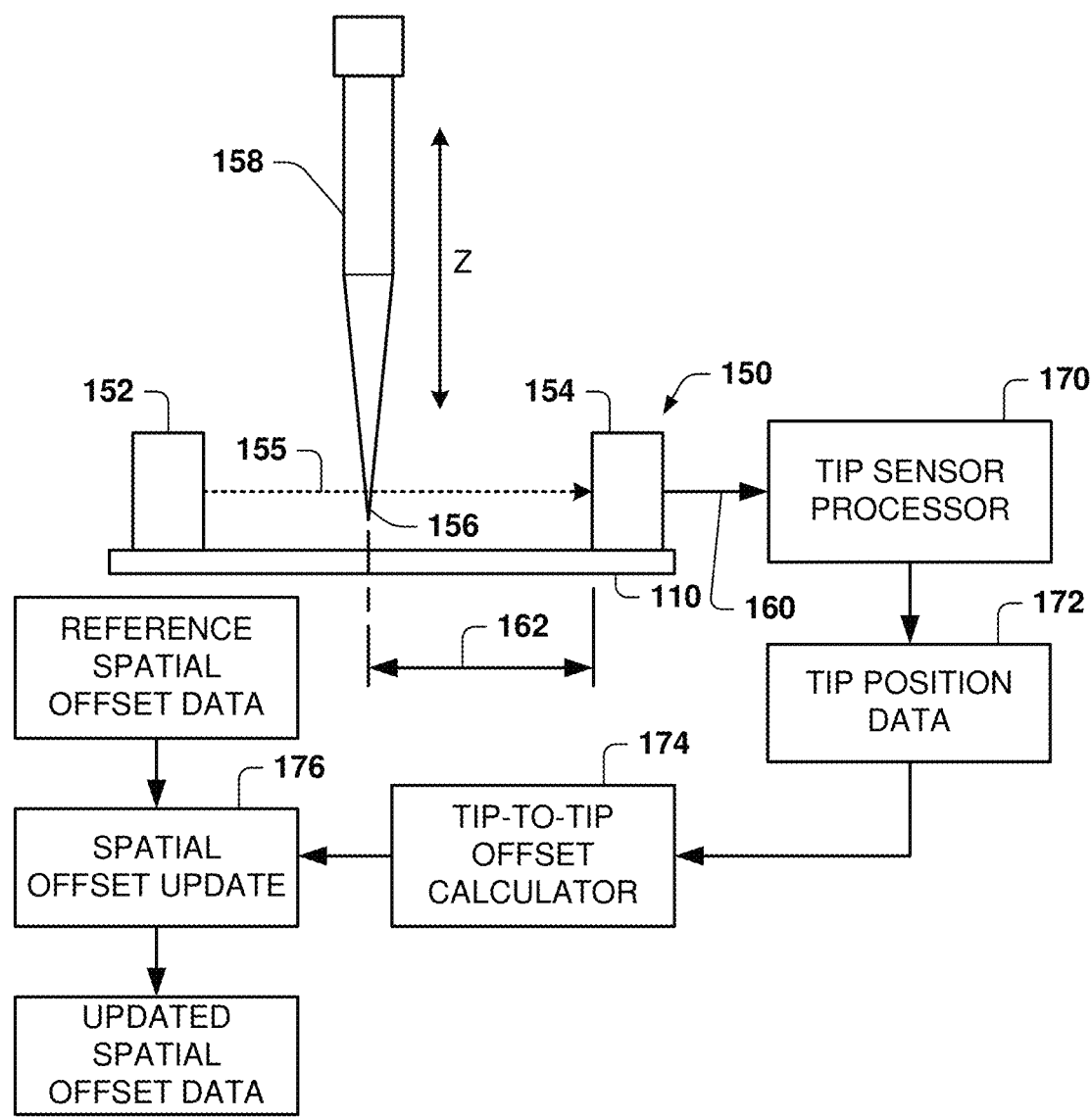
FIG. 8 depicts an example of a non contact tip sensing system that can be utilized for detecting the tip location with respect to axes of the stage.

FIG. 8 demonstrates a further example of identifying the tip location with respect to one of the X and Y axes. In the example of FIG. 8, the tip sensor 150 includes an optical transmitter 152 and optical receiver 154. The optical transmitter can transmit a beam of light (e.g., laser) 155 above the surface 122 of the stage 110 that is detected at the receiver 154. As the tip is spaced in the Z direction a predetermined distance above the stage 110 on which the sensor 150 is fixed, the stage can be moved in a direction orthogonal to the beam (along one of the X or Y axes) so that a distal end 156 of the tip 158 disrupts the beam. The disruption of the beam generates a tip sensor signal 160 to trigger recording respective coordinates for each beam for the axis that extends orthogonal to the beam. The coordinates of each beam may be known with respect to the X and Y coordinates of the stage or the beam coordinates may be relative to predetermined reference coordinates of the stage. Either way, the position information provided by each of the sensors 142 and 144 can be utilized to provide the position of each tip, which can be utilized to ascertain a precise tip offset between any two tips based on stage coordinates recorded when each beam is interrupted during the tip sensing phase.

Additionally, since the distance 162 can be determined in the absence of the distal end of the tip contacting the stage 110 or another structure disposed on the stage, there is a risk of contamination 156 through such location process. FIG. 8 also demonstrates a block diagram that can be utilized to determine the tip-to-tip offset as well as the corresponding spatial offset between the tip location and the optical access of the imaging system.

As a further example, a tip sensor processor 170 receives the tip sensor signal 160 to ascertain corresponding tip position along a given one of the X or Y axis. It is understood that each of the sensors 142 and 144 can implement similar processing to ascertain the tip location along the X and Y axes. In some examples, the tip sensor processing can also determine the distance 162 that can be combined with the known location of the tip sensor with respect to the X and Y coordinates of the stage 110 to provide absolute position data 172 for the X and Y position depending on which sensor 142 or 144 has detected the positioning of the tip 158. The tip position data 172 can store tip position for one or more tips that are utilized, such as including the reference tip position and the position of each subsequent tip that is being sensed by the system 150.

A tip-to-tip offset calculator 174 thus can compute the tip-to-tip offset based on the tip position data for the reference tip and another tip. The tip-to-tip offset can in turn be provided to a spatial offset update function 176. The spatial offset update can aggregate the reference spatial offset that is stored in memory with the tip-to-tip offset that has been calculated to in turn provide the updated spatial offset data that can be stored in memory and in turn utilize to position the tip 158 with respect to a desired target object that has been identified in the field of view of a captured image.

In addition to calibrating the position of the tip with respect to X and Y coordinates of the stage 110, systems and methods disclosed herein can be implemented to calibrate the tip position with respect to the Z axis, which is orthogonal to the X and Y axes of the stage. The Z axis calibration thus can relate a height of the distal end of the tip with respect to the surface of the stage to further facilitate controlling interaction with one or more objects that may reside in a medium positioned on a surface of the stage. For example, plates that may be positioned on the surface of the stage may have non-uniform thicknesses as well as other topographical variations across the surface thereof that may need to be accounted for. Additionally or alternatively, different tips that can be positioned onto the tool, such as disclosed herein, for picking and/or for placing objects with respect to the stage. When attached to the tool, each of the different tips can provide spatial variations in the Z direction as well as the X and Y directions, even when the tips are of the same size and design. These and other variations, if not accounted for, can result in errors when interacting with objects at various locations on the stage.

Figure 9:
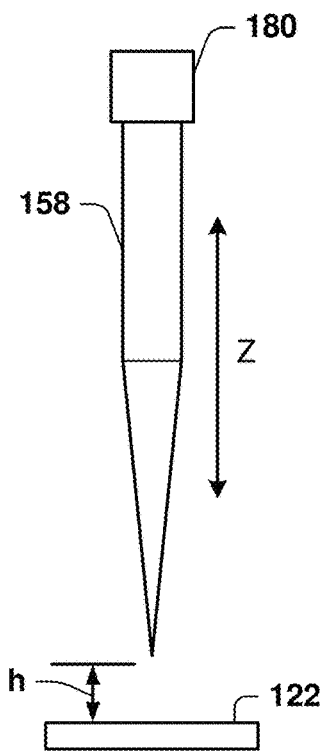
FIGS. 9 and 10 depict examples of a Z-axis sensor to detect tip height along the Z axis.
Figure 10:
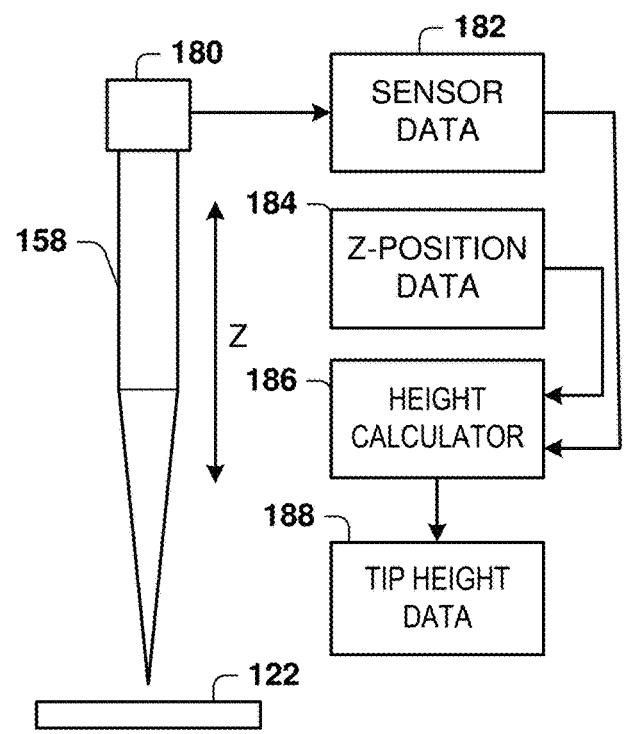

FIGS. 9 and 10 depict an example of an approach that can be utilized to determine height of a tip 158 with respect to a local region of the stage or other object that may be positioned on a surface of the stage 122. As mentioned the surface of the stage may or may not be planar surface. The calibration along the Z axis can be utilized to reconcile small (e.g., micron level differences) between a plane of the tip and a surface plane of the stage to enable precise control of the height of the tip with respect to the surface of the stage. In the example of FIG. 9, the tip 158 is positioned a distance "h" above the surface 122 of the stage or an object positioned on the stage. A sensor 180 is implemented to detect force applied to the tip in the Z direction (e.g., along the Z axis of the tip 158).

By way of example, the force sensor 180 can be implemented as part of the tool, such as integrated into the tip holder, via mount system to insure adequate sensitivity along the Z axis. In other examples, the force sensor 180 might be a strain gauge that is part of the tool or integrated into the tip itself. As another example, the sensor could be positioned on the stage or be implemented partially on the tip or tool and partially on the stage to provide information to determine Z axis height in reference to the bottom of the sample plate. The force sensor 180 operates as a highly sensitive scale measuring the weight of the smart syringe, such that any pressure applied either up or down provides a corresponding output indicative of the sensed force. The force sensor signal can be provided to the control system via a communications link. For example, the communications link may be a wireless link (e.g., Bluetooth or other short range wireless communications technology) or a physical link (e.g., optical or electrically conductive cable). The force sensor output can be stored in memory as force sensor output data 182 for processing to ascertain the z-axis position of the tip 158.

The control system 40 is programmed to determine the height of the tip based on the force sensor data and Z-position data 184 obtained during a Z axis calibration mode. For example, tip 158 begins at a start position where Z-axis position data 184 is recorded based on an output of a Z-axis encoder associated with the tool. The control system 40 provides tool motion control instructions to move the tip in the Z direction toward the surface 122. The distal end of the tip traverses a distance from its start position up to a distance corresponding to the height of the tip from the stage, producing corresponding Z-position data during such movement. In response to the distal end of the tip 158 contacting the surface 122, the force sensor 180 can provide a corresponding signal representing the sensed force, which indicates contact between the tip and the solid surface. A height calculator 186 (e.g., of the control system 40) computes the distance of travel, corresponding to tip height data 188, based on a difference between the Z position data 184 at the start position (FIG. 9) and the Z position data when contact occurs (FIG. 10). For example, the contact can be ascertained from the force data 182 indicating sufficient force to indicate a solid object, such as the surface 122, and not a fluid medium disposed thereon. That is, the control system 40 can discriminate between contact with a solid surface and a fluid medium.

Figure 11:
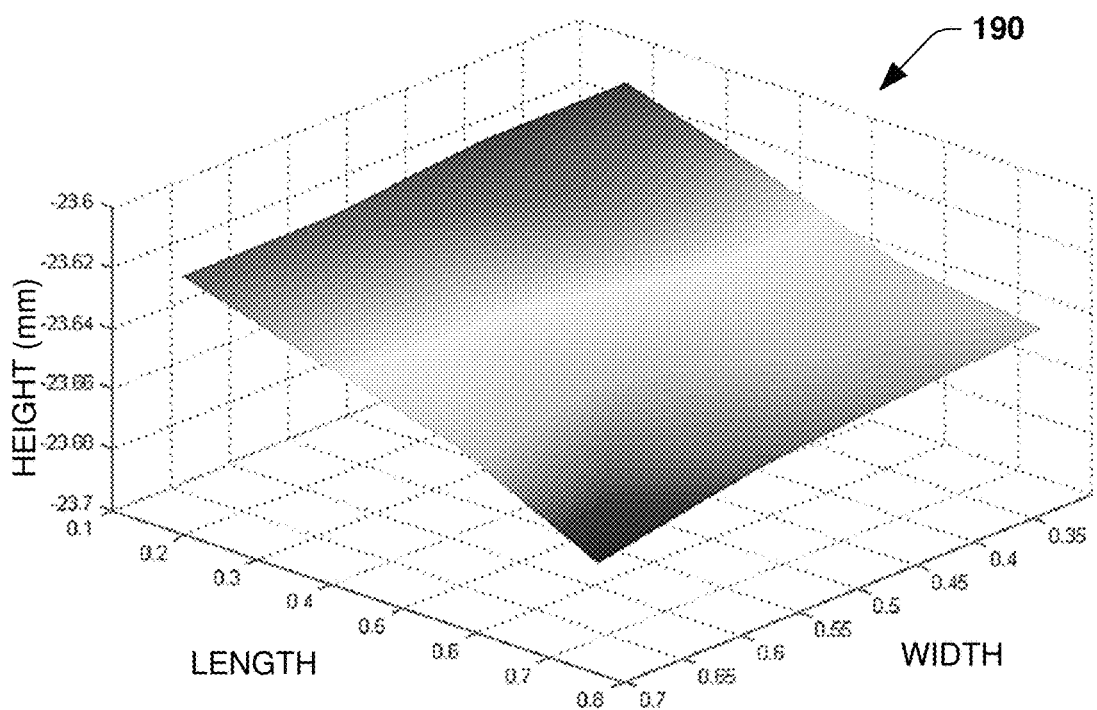
FIG. 11 depicts an example of a topographical map of a surface that can be detected using the tip height sensing of FIGS. 9 and 10.

In addition to the tip height data specifying the distance 178 between the tip and the surface 122, the tip height data can also specify the X and Y coordinates (e.g., stage coordinates) where the tip height is measured (e.g., a tip height measurement location). The tip height data, including the height in the Z direction and associated X, Y coordinates for such location, can be stored in memory for a plurality of X, Y coordinates across the surface of the stage. The tip height data 188 can be utilized to provide a corresponding topographical map of the surface of the stage 122 or other object disposed thereon for one or more portions of the surface on the stage, such as shown in FIG. 11. For example, the tip height can be utilized to create a topographical surface map based on measuring height for one or more locations across the surface of the stage, which tip height measurements and associated measurement locations (e.g., in stage X,Y coordinates) can be stored in memory.

FIG. 11 demonstrates an example of a topographical map with a surface, such as an unoccupied surface of a well plate that is positioned on the stage 110. It is understood that such a detailed map is not required for the entire surface sense the tip plate is only relevant or needed for locations adjacent to each target site.

The control system 40 can employ the stored tip height measurements to control the tip height at or near one or more desired locations on the surface 122 such as for interacting with objects that have been identified in the corresponding image. For example, prior to each interaction at a specified X,Y coordinate (e.g., determined from image analysis 24 as disclosed herein), the Z axis tip height calculator 186 of calibration function 54 can be utilized to determine the height of the tip (e.g., corresponding to the distance of the Z-direction between the tip and the surface 122) at a location that is adjacent to but spaced apart from the target site. Similarly, the corresponding tip height ascertained at the adjacent location or a series of adjacent locations can be utilized to specify the tip height as to control the interaction with objects at each respective target site. If the tip height is already known at a measurement location that is within a predetermined distance of a target site, the known tip height can be utilized to control the interaction at each target site that is within such predetermined distance. By determining tip height at one or more measurement locations adjacent to a target site, the height of the tip can be controlled precisely during interaction at the target site without having to potentially damage the object at the target site.

Figure 12:
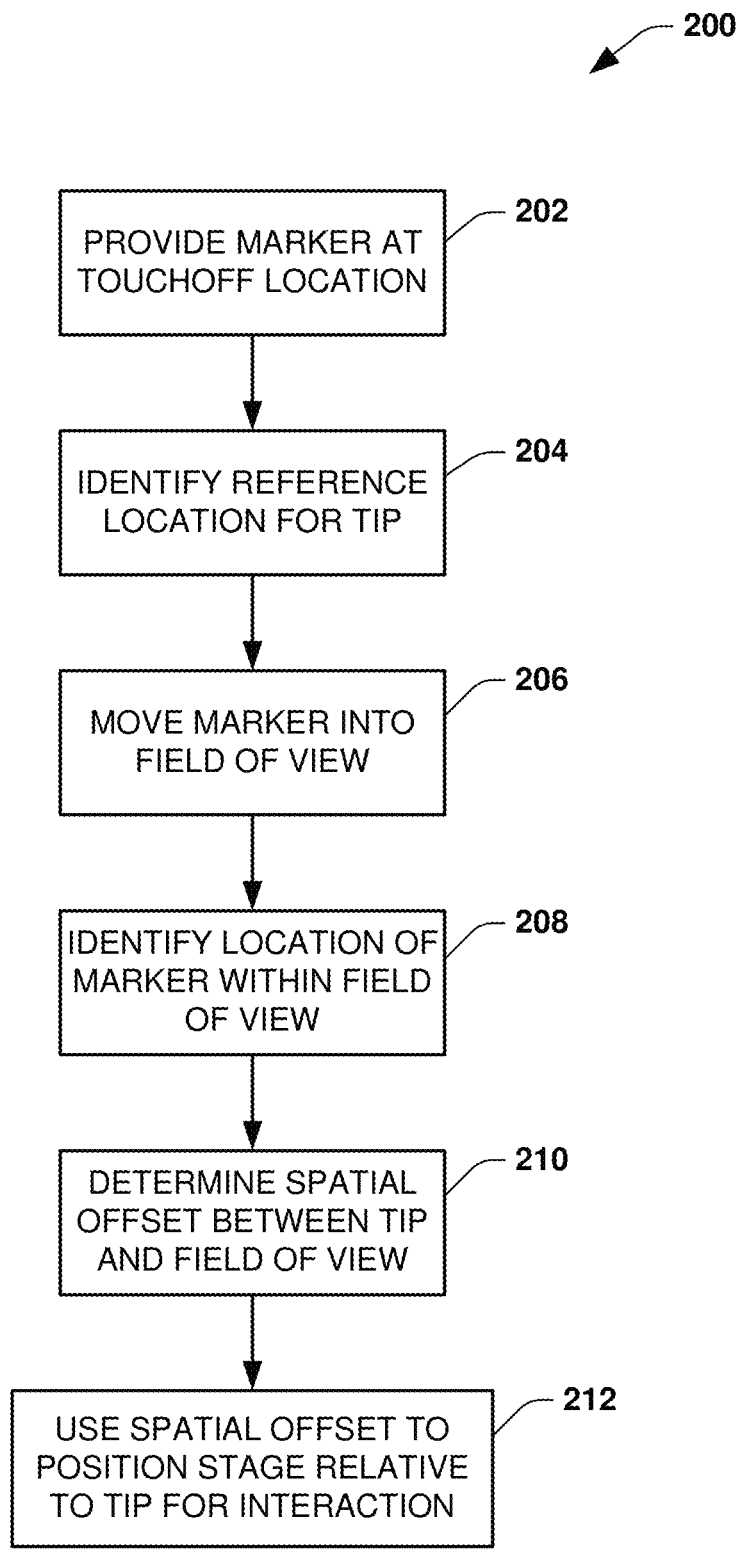
FIG. 12 is a flow diagram depicting an example of a calibration method.
Figure 13:
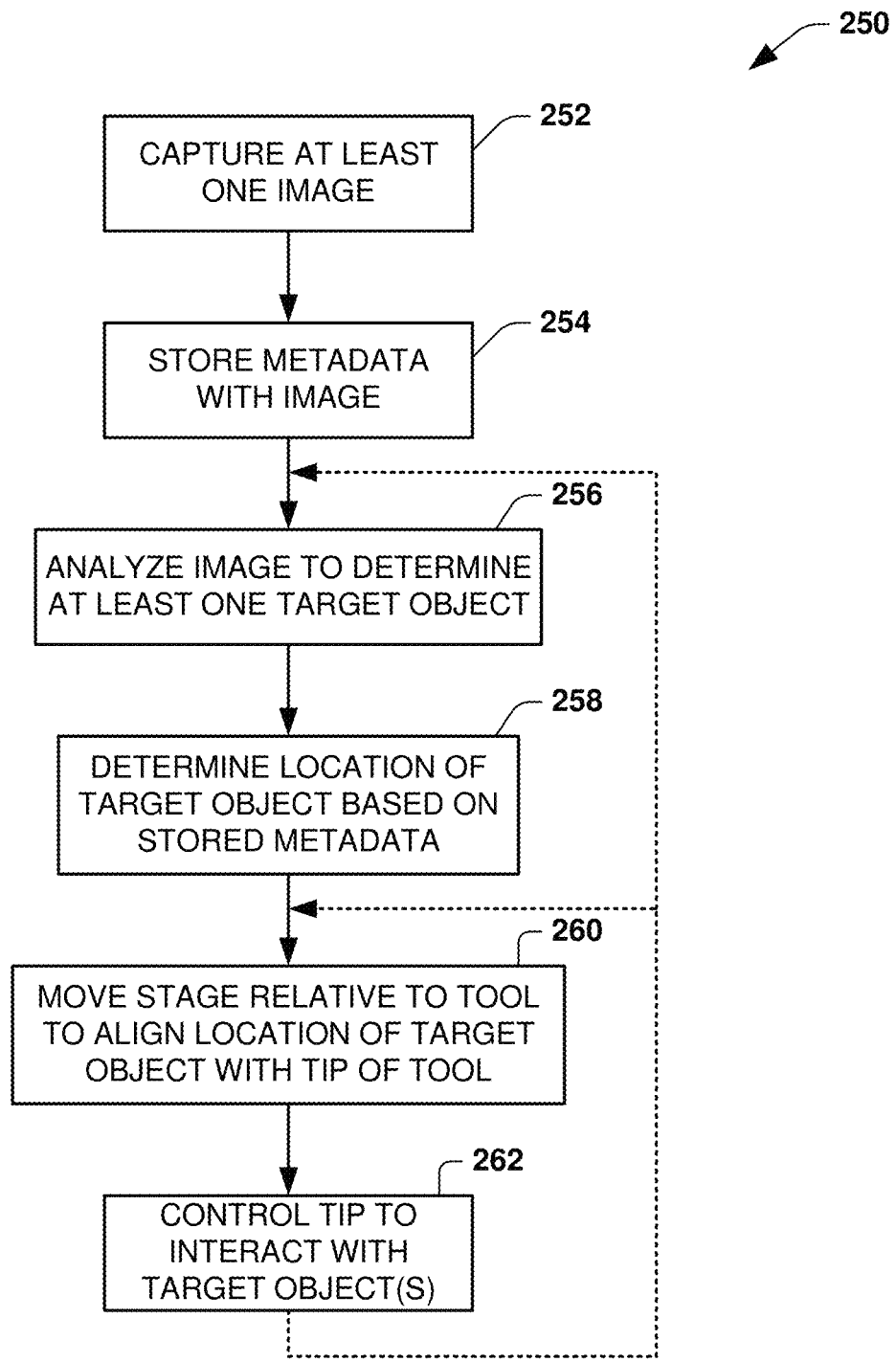
FIG. 13 depicts an example of a method for interacting with an object identified in an image.
Figure 14:
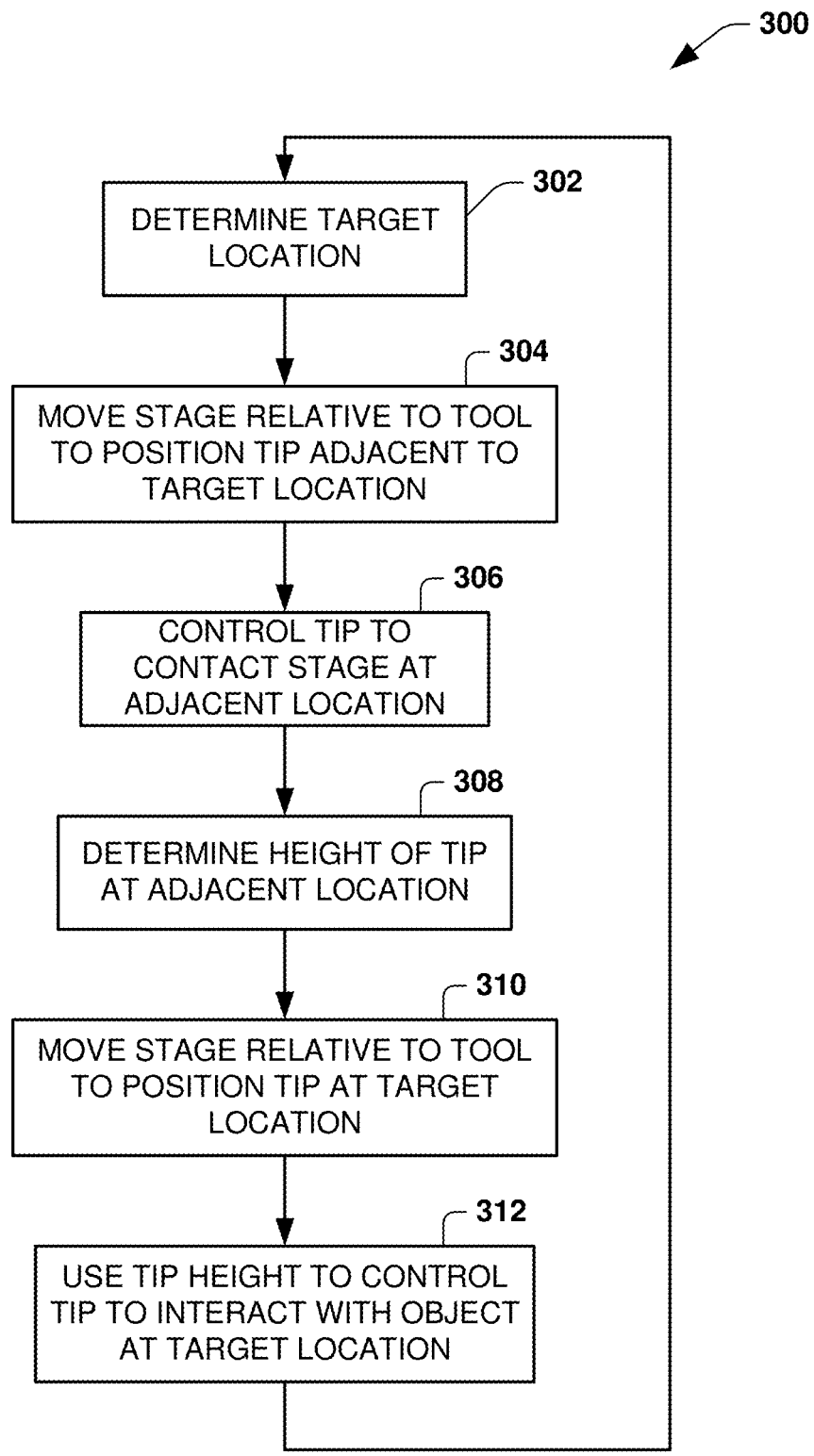
FIG. 14 depicts an example of a method to determine the tip height in association with and identifying a location of an image to enable interaction with the object.

In view of the foregoing structural and functional features described above, methods that can be implemented will be better appreciated with reference to FIGS. 12-14. While, for purposes of simplicity of explanation, the methods of FIGS. 12-14 are shown and described as executing serially, it is to be understood and appreciated that such methods may not be limited by the illustrated order, as some aspects could occur in different orders and/or concurrently with other aspects from that shown and described herein. Moreover, not all illustrated features may be required to implement a method. The methods or portions thereof can be implemented as instructions stored in a non-transitory storage medium as well as be executed by a processor of a computer device, for example. Additionally, in some implementation, two or more of the methods of FIGS. 12-14 (or portions of two or more such methods) may be combined together as part of a workflow for calibrating and/or implementing an interaction protocol.

FIG. 12 depicts an example of a calibration method 200 to facilitate positioning a stage to provide for interaction between a tip and one or more objects identified in an image. The method 200 begins at 202 in which a marker is provided at a touchoff location. For example, a corresponding tool can be moved to a predefined reference position and moved in the Z-direction to contact the surface of the stage and place a marker at such touchoff location in response to such contact. The marker can be ink or any other substance that may be visible via the imaging system (e.g., system 20 of FIG. 1). At 204, a reference location for the tip can be identified. For example, the reference location for the tip can corresponding to the coordinates of the movable stage (e.g., stage 12 or 110) in two or more dimensions such as according to positions provided by encoders for the X,Y directions for linear actuators that are employed for adjusting the position of the stage.

At 206, the marker is moved into the field of view of the imaging device. For example, the stage position can be adjusted to align the marker within a field of view from the imaging system (e.g., camera) that is positioned orthogonally and spaced apart from the surface of the stage onto which the marker is provided at 202. The movement of the marker to a prescribed position within the field of view can be implemented manually (in response to user inputs), automatically or can employ a combination of manual and automatic motion controls.

At 208, the location of the marker within the field of view can be identified. For example, the location of the marker within the field of view can be identified based on the coordinates (e.g., X,Y position) of the stage after the marker has been moved into the field of view at 206. The identified location can itself be the X,Y position of the stage or it can be the X,Y position of the stage in combination with distance between one or more pixels that represent the marker in an image captured by the image device relative to an optical reference in the image.

For example, the optical reference in the image can correspond to a center of the field of view for the captured image or to one or more pixels at the periphery at such captured images. For instance, if the marker is moved into alignment at the Z-direction with the reference pixel or pixels in the field of view, then the identified location at 208 can represent the position of the stage. Otherwise the pixel distance can be applied to the position of the stage to represent the location of the marker within the field of view.

At 210, the spatial offset between reference location for the tip and the field of view is determined. The spatial offset can be determined, for example, based on a difference between the identified location for the tip at 204 and the identified location for the marker at 208. The spatial offset for the tip and the field of view can be stored in memory as an optical offset that is utilized at 212 to position the stage relative to the tip for any number of one or more subsequent interactions between the tip and objects on the stage. For example, the control system can apply the spatial offset to move the stage so that any object identified in any captured image can be aligned with respect to the tip to enable interactions between the tip and such identified objects. As disclosed herein, the interactions can include one or more of cutting material from the stage (e.g., from a well plate), scraping material, stamping material on the stage, stirring or agitating a medium on the tray or aspirating (e.g., picking) objects from the tray and/or transferring objects to one or more destinations on the stage or elsewhere.

FIG. 13 depicts an example of a method 250 to control interaction with objects. The method 250 begins at 252 with capturing one or more images via the imaging device (e.g., imaging system 20). The captured image can be for a field of view on the surface of the stage (e.g., stage 12 or 110) such as including various objects, including biological objects or the like that may be disposed within well plates as is known in the art. For each image that is captured at 252 metadata is stored with the image at 254 (e.g., metadata 23 embedded in or otherwise associated with image data 22). The metadata includes position of the stage at the time of each image as well as the indication of image resolution for each captured image. The image resolution and stage position thus can be utilized to ascertain an absolute position in the X,Y coordinates of the stage for each pixel in each captured image. For instance, one or more reference pixels in a given image (e.g., a center location and/or a location on a periphery image) can be used as reference pixels that have a known position with respect to the coordinates of the stage. Since the resolution is known, each pixel can be assigned a dimension such that the number of pixels between the reference position can be utilized to ascertain a relative or absolute position with respect to the X,Y coordinates of the stage. While the foregoing has been described as two-dimensional image, similar metadata can be provided for a three-dimensional image.

At 256, the captured image can be analyzed to determine one or more target objects in the image. For example, the image analysis at 256 can be implemented according to the above-incorporated U.S. Pat. No. 8,068,670. Those skilled in the art may understand and appreciate other image analysis techniques that may be utilized to detect target objects on the stage. At 258, the location of the target object is determined based on the stored metadata for the captured image that was analyzed of one or more objects.

At 260, the stage can be moved relative to the tool to align the location of the target object or objects with the tip of the tool. For example, the control system (e.g., stage motion control 44) can control the motion of the stage along each of the X,Y positions to align the tip position with the target object. If the target object is larger than the tip of the tool, and the interaction is to occur over a spatial area that involves multiple sequential interactions, a corresponding interaction protocol, such as disclosed herein can be utilized to control the stage to move to a sequence of locations for tip alignment and corresponding interaction at each of the sequential locations distributed across the surface area of the identified object.

At 262, the tip can be controlled to interact with the object such as by controlling motion of the tip along the Z axis to a location that is spaced apart from the contact surface of the stage or plate that may be positioned thereon and the corresponding interaction may then be activated according to the selected interaction protocol. As one example, the hollow tip can be inserted into a medium and aspirated and draw in a volume of media and corresponding biological objects growing therein. This may be repeated at the plurality of sequential locations as disclosed herein. Other forms of interaction disclosed herein can be performed at the identified locations disclosed herein.

From 262, the method may return to 256 to further analyze one or more of the images to determine additional target objects for which interaction may be desired and the method may proceed accordingly. Alternatively, the method can proceed from 262 to 260 to in turn move the stage to a subsequent sequential location to align the tip of the tool with another part of the target object to enable the interaction at 262 for each of the subsequent sequential locations that have been specified. For each positioning of the stage with respect to objects in an image, the metadata of the image is utilized for such positioning. The method can repeat until the procedure has been completed according to the selected interaction protocol(s).

FIG. 14 depicts an example of another method 300 that can be utilized to facilitate positioning a tip with respect to the stage along the Z axis. The method 300 can be considered a Z axis calibration method, for example. The method 300 begins at 302 in which a target location is determined. The target location can be determined by specifying coordinates, such as may be determined from image analysis (e.g., analysis 24) performed for one or more captured image or may otherwise be identified. The target location for example, may include biological or other objects of interest, such as art to be picked from a media residing on the stage. In some examples, target objects can be considered objects that are to be destroyed and removed from the stage to allow further growth and culture of desired biological objects.

At 304, the stage is moved relative to the tool to position the tip adjacent to but spaced from the target location determined at 302. The adjacent location can be free from the desired target object, such as in situations where it is desired not to contact the objects during calibration. For example, where a colony of cells have been identified on the stage within a given surface location, an adjacent portion of the stage can be defined as the adjacent area (e.g., positioned greater than 10 microns, such as about 50-100 microns from the identified target location) to which the tip can be aligned by movement of the stage at 304.

At 306, the tip can be controlled to contact the stage at such adjacent location. For example, a corresponding linear actuator can be controlled to move the tool and the tip that is attached thereto in the direction of the stage until contact between the tip and stage is detected (e.g., by Z-axis force sensor 180). At 308, the difference between the starting position and the tip and the distance traveled in the Z-direction (e.g., as measured by a Z-axis encoder) can be employed to determine the height of the tip at the adjacent measurement location. Since the adjacent measurement location is sufficiently close although spaced from the target object location, it is assumed that the variation in the surface of the stage or other contained object disposed thereon will be relatively small. A threshold for the adjacent measurement location can be preset or user defined according to application requirements, such as in response to a user input. Thus, after Z-axis calibration for tip height at the adjacent measurement location, at 310, the stage can be moved relative to the tool to position the tip aligned axially with the target location.

At 312, the tip height determined at 308 can be utilized to control the tip to interact with the object and/or medium at the target location in a desired manner according to a selected interaction protocol. For example, since the height of the tip is known at the adjacent measurement location, the interaction protocol can use that height to ensure that the tip is not moved in the Z-direction, unless that is required by the interaction protocol. The method 300 can return from 312 to 302 to repeat 304-312 for each subsequent target location as part of the interaction protocol. In some cases, where the next target location are considered sufficiently close to the adjacent measurement location where the height was determined at 308, from 312 the method can instead return to 310 to remove the tip of the tool to the next target location and employ the same tip height over a plurality of interaction.

Figure 15:
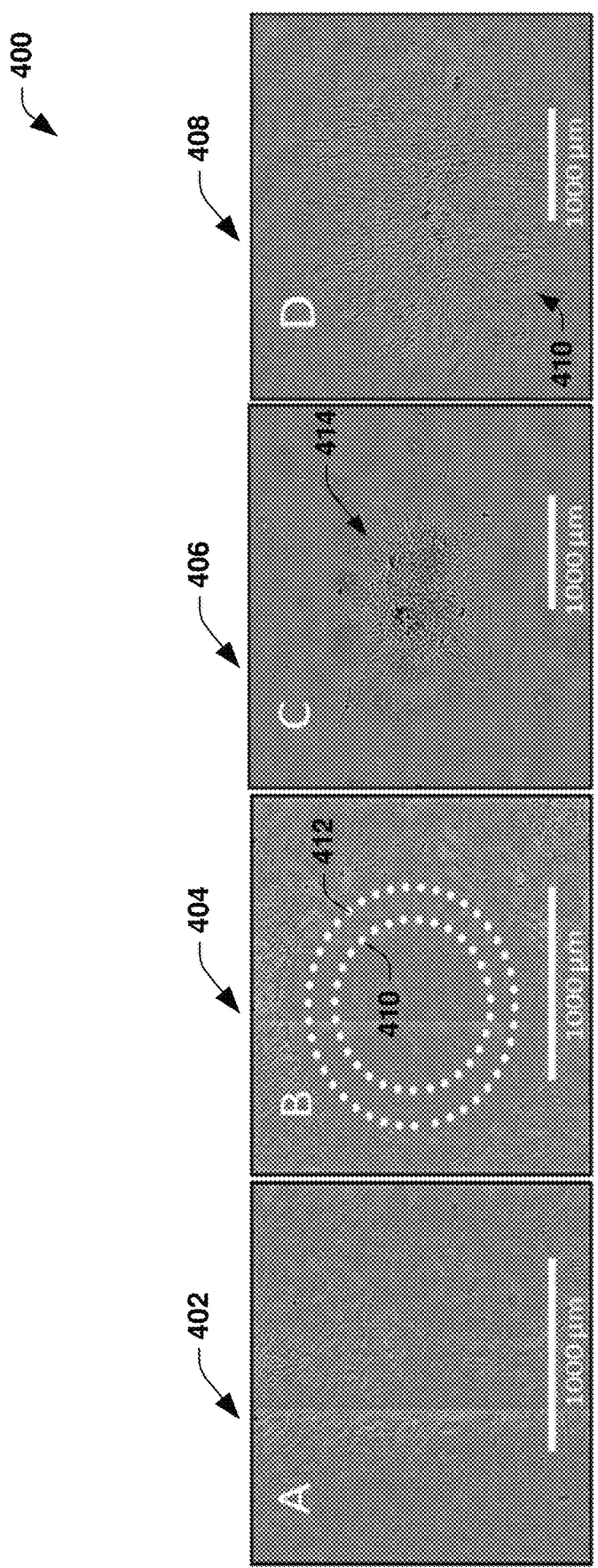
FIG. 15 depicts examples of images of objects on a stage associated with a sequence of interactions for transferring identified biological objects.

FIG. 15 depicts an example of captured images 402, 404, 406 and 408 demonstrating different steps of an interaction protocol associated with monolayer picking. For example, the captured image 402 corresponds to a source location in which a plurality of objects of interest have been identified such as corresponding to a colony of area. For example, the object of interest can be identified by image analysis (e.g., analysis 24) such as can include the colony area, colony density, cell number, cell marker area expression or a combination thereof. The captured image 404 demonstrates the source location for the object of interest following biopsy of the cells, such as using a tip and aspirating from the source location containing the desired target objects. In image 404, inner and outer diameters of the harvest tool are demonstrated as concentric rings 410 and 412, respectively. The captured image 406 demonstrates the cells after being transferred to a different location for which the captured image 406 was obtained for a corresponding field of view. The cells for example demonstrate growth for the transferred cells for a period of about 24 hours. The image 408 demonstrates the transferred cells at a later time period (e.g., about six days).

Figure 16A:
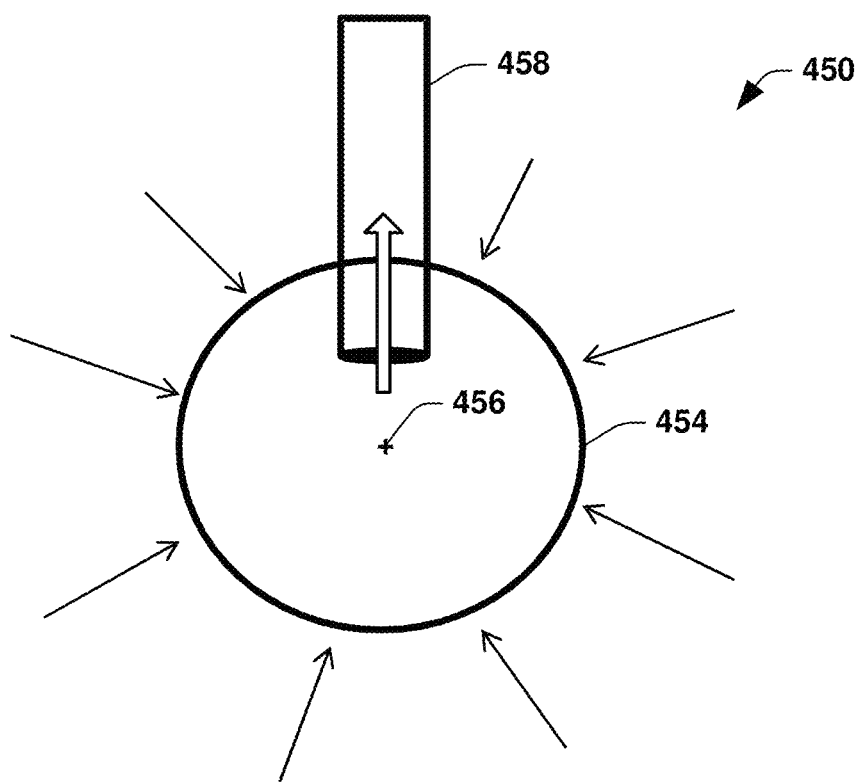
FIGS. 16A and 16B depict an example of another harvest sequence of interactions that can be implemented.
Figure 16B:
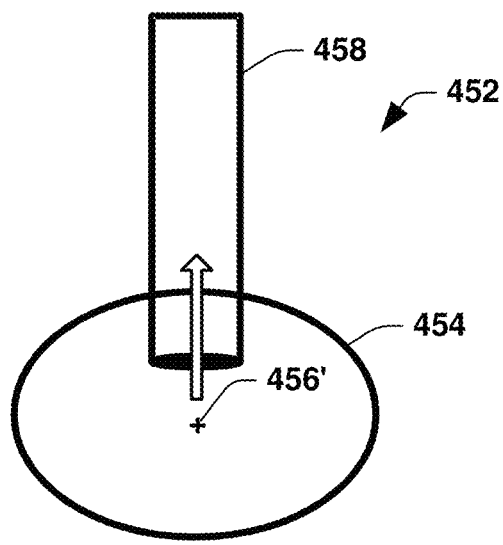

FIGS. 16A and 16B depict a schematic illustration of first and second aspirations performed for an object, demonstrated at 450 and 452. The syringe motion and/or stage motion systems can cooperate to position a tip 458 of a hollow needle for each aspiration. For the first aspiration 450, for example, where an object (e.g., a colony) 454 is disposed in a two-dimensional medium, an initial centroid 456 for the object can be computed (e.g., by image analysis 24). Corresponding process parameters for a selected interaction protocol can be applied based on the relevant data (e.g., image data, sensor data, syringe motion data, aspiration data) to control the first aspiration that is performed by positioning the tip 458 into the medium at the centroid 456 spaced a distance.

Following the first aspiration (FIG. 16A), the colony geometry can shift such as demonstrated schematically at 452 in FIG. 16B. Prior to performing the second aspiration, process parameters can be recomputed and stored at least in part as updated aspiration data for the next aspiration. For instance, this can include computing (e.g., by the image analysis 24) a new centroid 456' of the remaining target object based on the updated image data that is captured by moving the target object 454 into the field of view of the image capture device (e.g., camera 60). The tool function control of the control system 40 can employ the updated process parameters to perform the second aspiration according to the selected protocol. This process can be repeated until harvesting has been completed for the target object.

Figure 17:
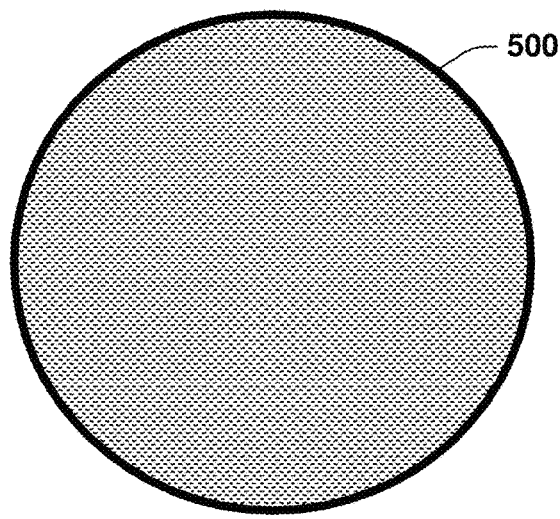
FIG. 17 depicts example of part of an interaction protocol for harvesting biological objects that is updated dynamically based on post-interaction image data.
Figure 17:
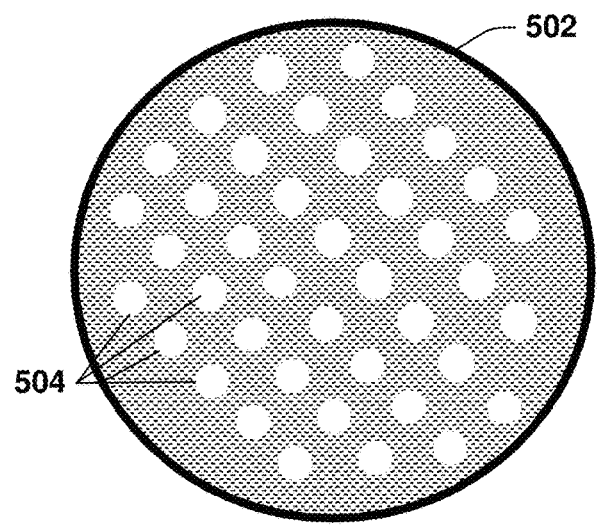
Figure 17:
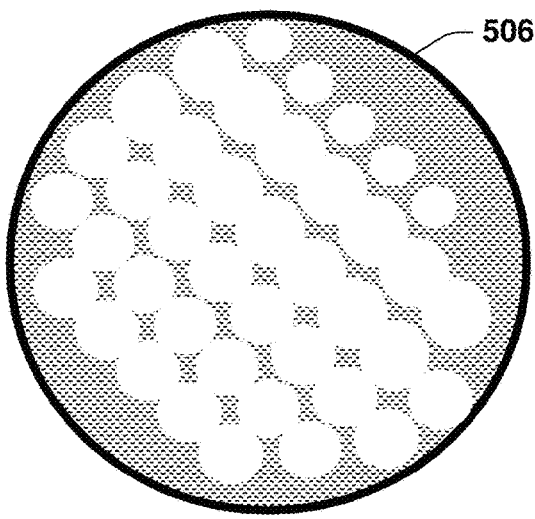
Figure 17:
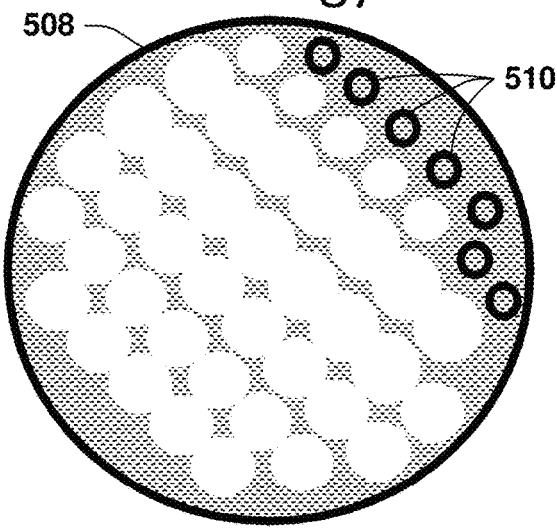

As another example, FIG. 17 demonstrates another approach that can be utilized for harvesting cells from a colony according to a selected interaction protocol. For instance, an original colony object can be identified based on the image analysis, as demonstrated at 500. Based on the image analysis, the aspiration tool and fluidic controls can compute an initial (e.g., original) harvest strategy 502. The harvest strategy 502 can include a plurality of target sites 504 at which aspiration is to be performed sequentially as well other process parameters for controlling aspiration at each of the sites. Following the initial/original harvesting at the sites 504, the colony object can be moved to within the field of view of the imaging system to acquire image data (e.g., one or more images) representing the current state of the colony object, shown at 506. The corresponding image data can be utilized to compute a second, updated harvest strategy 508 to facilitate harvesting remaining cells in the colony object at new target sites, such as shown at 510. While in this example, the second harvest strategy is computed after completion of the first strategy, it will be appreciated that the harvest strategy can be variable and dynamically updated based on image data acquired during any number of sequences of aspiration specified by the interaction protocol.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A system comprising:
a stage;
a stage motion system adapted to move the stage along orthogonal axes of the stage;
a tool holder supporting a tool above a surface of the stage, wherein the tool includes a body extending toward the stage and terminating in a distal end thereof, wherein the distal end of the tool body is configured to support a given tip of a plurality of tips, and each of the plurality of tips is replaceable on the distal end of the tool body;
a tool motion system configured to position the tool relative to the stage;
a tip position sensor fixed with respect to the surface of the stage and configured to provide first tip position data representing a tip location of the given tip of the plurality of tips with respect to at least one orthogonal axis of the stage when the tool is positioned at a reference position, wherein in response to replacing the given tip of the plurality of tips with an other tip of the plurality of tips, the other tip has a tip location different than the given tip with respect to the at least one orthogonal axis of the stage; and
a control system configured to:
control the tool motion system to position the tool at the reference position while the tool body supports the other tip;
control the tip position sensor to detect a spatial location of the other tip and provide second tip position data representing the tip location of the other tip when the tool is positioned at the reference position;
determine a tip-to-tip offset between the tip location of the given tip and the tip location of the other tip based on the first and second tip position data;
aggregate the tip-to-tip offset with a predetermined spatial offset to provide an aggregated spatial offset representative of a spatial offset between the other tip and an optical location within a field of view (FOV) of an imaging device having a known spatial position relative to the stage, the predetermined spatial offset being representative of a spatial offset between the given tip and the optical location; and
control the stage motion system to position the stage relative to the other tip based on the aggregated spatial offset to enable the other tip to interact with a target location on the stage identified in one or more images provided by the imaging device.

2. The system of claim 1, wherein the tip position sensor further comprises:
an optical transmitter configured to transmit a beam of light; and
an optical receiver configured to receive the beam of light, the given tip being spaced apart from the surface of the stage at a predetermined distance, the stage being configured to move in the at least one orthogonal axis of the stage orthogonal to the beam, such that a distal end of the given tip disrupts the beam to generate the first tip position data, wherein in response to replacing the given tip with the other tip, the other tip being spaced apart from the surface of the stage at the predetermined distance, the stage being configured to move in the at least one orthogonal axis of the stage orthogonal to the beam, such that a distal end of the other tip disrupts the beam to generate the second tip position data.

3. The system of claim 1, wherein the control system is configured to:
control the stage motion system to position the stage at a plurality of different positions along the orthogonal axes of the stage;
receive stage position data representing the position of the stage in the orthogonal axes of the stage
identify respective spatial locations based on the stage position data; and
determine the predetermined spatial offset based on the respective spatial locations.

4. The system of claim 3, wherein the imaging device is associated with the stage and spaced apart from the tool, wherein the stage motion system is configured to:
position the stage at a first position of the plurality of different positions to position a visible mark on the surface of the stage outside the FOV of the imaging device; and
position the stage at a second position of the plurality of different positions to position the visible mark in the FOV of the imaging device.

5. The system of claim 4, wherein the control system is configured to:
identify first spatial coordinates for the visible mark in the orthogonal axes of the stage in response to the stage being positioned at the first position;
cause the imaging device to capture at least one image for the FOV in response to positioning the visible mark within the FOV of the imaging device;
identify the optical location associated with at least one pixel in the FOV based on the at least one image, wherein the optical location is associated with respective spatial coordinates in the orthogonal axes of the stage corresponding to second spatial coordinates; and
identify the second spatial coordinates for the visible mark with respect to the orthogonal axes of the stage based on the optical location in response to the stage being positioned at the second position, wherein the predetermined spatial offset is determined based on the first and second spatial coordinates.

6. The system of claim 5, wherein the other tip of the tool comprises a marker, wherein the control system is configured to position the other tip of the tool relative to the stage to contact the surface of the stage to transfer the marker to provide the visible mark on the surface of the stage in response to the stage being positioned at the first position, the first spatial coordinates being identified based on the stage position data in response to the stage being positioned at the first position, and the second spatial coordinates being identified based on the stage position data in response to the stage being positioned at the second position.

7. The system of claim 6, wherein the control system is configured to position the stage relative to the other tip further based on a tip height for the other tip to enable the other tip to interact with the target location on the stage.

8. The system of claim 7, wherein the tool motion system is configured to move the tool relative to the stage along an axis that is orthogonal to the surface of the stage to enable the other tip to contact the surface of the stage or an object at the target location on the surface of the stage, the system further comprising a contact sensor to detect the contact between the other tip and the stage or the object on the surface of the stage.

9. The system of claim 8, wherein, prior to interaction with the target location on the surface of the stage, the control system is configured to:

identify first tip spatial coordinates for the other tip of the tool in the at least one orthogonal axis of the stage in response to the tool being positioned at a given location relative to the stage;

cause the tool motion system to move the other tip of the tool along the axis that is orthogonal to the surface of the stage to contact the surface of the stage at the given location that is adjacent to but spaced from the target location on the stage, wherein the contact sensor is to generate a corresponding signal indicative of contact between the other tip of the tool at the surface of the stage at the given location;

identify second tip spatial coordinates for the other tip of the tool in the at least one orthogonal axis of the stage based on the corresponding signal; and determine the tip height of the other tip based on the first and second tip spatial coordinates, the control system being configured to control the interaction of the other tip with the target location on the surface of the stage further based on the tip height.

10. The system of claim 9, wherein the control system is configured to cause the other tip of the tool to interact with one or more objects of interest at the target location based on the aggregated spatial offset and the tip height, the interaction includes at least one of adding one or similar or different objects to the objects at the target location, removing the one or more objects of interest at the target location, applying a fluid to the one or more objects of interest, removing fluid applied to the one or more objects of interest, dislodging the one or more objects of interest to separate the one or more objects from at least one other object at the target location, moving the one or more objects of interest at the target location to a location on the stage different from the target location, stamping the one or more objects of interest, stirring a medium in which the one or more objects are disposed in at the target location, aspirating the one or more objects from the stage, scraping the one or objects of interest.

* * * * *